United States Patent
Yamada et al.

(10) Patent No.: US 11,226,329 B2
(45) Date of Patent: Jan. 18, 2022

(54) EXHALED GAS DETECTOR AND EXHALED GAS DETECTION METHOD

(71) Applicant: HITACHI, LTD., Tokyo (JP)

(72) Inventors: Masuyoshi Yamada, Tokyo (JP); Hironori Wakana, Tokyo (JP)

(73) Assignee: HITACHI, LTD., Tokyo (JP)

( * ) Notice: Subject to any disclaimer, the term of this patent is extended or adjusted under 35 U.S.C. 154(b) by 268 days.

(21) Appl. No.: 16/535,173

(22) Filed: Aug. 8, 2019

(65) Prior Publication Data

US 2020/0064331 A1 Feb. 27, 2020

(30) Foreign Application Priority Data

Aug. 27, 2018 (JP) .............................. JP2018-158785

(51) Int. Cl.
*G01N 33/497* (2006.01)

(52) U.S. Cl.
CPC ................ *G01N 33/4972* (2013.01)

(58) Field of Classification Search
CPC ............. G01N 33/4972; G01N 33/497; G01N 2033/4975; A61B 5/082
USPC ...................... 73/23.3, 1.06, 23.31
See application file for complete search history.

(56) References Cited

U.S. PATENT DOCUMENTS

2008/0316037 A1* 12/2008 Shoji .................. G01N 33/4972
340/576

FOREIGN PATENT DOCUMENTS

| JP | 2002-39881 A | 2/2002 |
| JP | 2004-245800 A | 9/2004 |
| JP | 2005-157599 A | 6/2005 |
| JP | 2009-31002 A | 2/2009 |
| JP | 2010-139319 A | 6/2010 |
| WO | 2017158846 A1 | 9/2017 |

OTHER PUBLICATIONS

Japanese Office Action received in corresponding Japanese Application No. 2018-158785 dated Nov. 16, 2021.

* cited by examiner

*Primary Examiner* — Robert R Raevis
(74) *Attorney, Agent, or Firm* — Mattingly & Malur, PC

(57) ABSTRACT

An exhaled gas detector includes: a gas detection element configured to measure a specific gas; and an analysis unit configured to analyze a signal output from the gas detection element. The gas detection element measures the specific gas in an exhalation of non-drinking time and generates a first reference signal value. The analysis unit calculates a first threshold value on the basis of the first reference signal value. The gas detection element measures the specific gas in an inspection gas and generates a first measurement signal value. The analysis unit determines that the inspection gas is identified with an exhalation of a person by determining that the first measurement signal value has exceeded the first threshold value.

11 Claims, 22 Drawing Sheets

EXHALED GAS DETECTOR AND EXHALED GAS DETECTION METHOD

CROSS-REFERENCE TO RELATED APPLICATIONS

This application is based upon and claims the benefit of priority from Japanese Patent Application No. 2018-158785 filed on Aug. 27, 2018; the entire contents of which are incorporated herein by reference.

BACKGROUND OF THE INVENTION

1. Field of the Invention

The present invention relates to a technology of an exhaled gas detector and an exhaled gas detection method for analyzing exhalation.

2. Description of the Related Art

In automatic operation of vehicles in the future, detection of drinking or non-drinking, condition of people, and the like is required in switching the automatic operation and manual operation. In particular, in detecting alcohol concentration in exhalation, there is a need for a technology for detecting human natural exhalation to prevent impersonation by introducing outside air into a device as if the outside air were exhalation.

In the market, needs for mobile-type detection terminals suitable for various use cases are expanding, and coping with mobile operation is required in the days ahead.

For example, WO 2017/158846 is disclosed as a technology for preventing drunk driving. WO 2017/158846 describes an exhaled gas detection device and an exhaled gas detection method, in which "the exhaled gas detection device includes, in order to accurately determine whether introduced outside air is exhalation of a person, a water vapor sensor (1) for detecting whether the introduced outside air contains saturated water vapor, and an analysis device for determining that the introduced outside air is the exhalation of a person on the basis of, for the introduced outside air, whether a signal value obtained from the water vapor sensor (1) has exceeded a predetermined threshold value, and a signal value obtained from a gas sensor (2) has exceeded a predetermined threshold value" (see summary).

SUMMARY OF THE INVENTION

Here, the inventors have found that the sensitivity of water vapor sensors and gas sensors differs depending on a person. That is, the inventors have found that a determination result as to whether a signal value by a water vapor sensor or a gas sensor has exceeded a threshold value differs depending on a person. The technology described in WO 2017/158846 gives no consideration to this point and further improvement is required.

Further, conventionally, determination of the threshold values has been dependent on experience or has been made on a case-by-case basis. However, the inventors have found that there are individual differences in output signals of the water vapor sensor and the gas sensor (in particular, maximum output voltages), and with the uniformly determined threshold values, determination results as to whether the output signals have exceeded the threshold values varies.

The present invention has been made in view of foregoing, and an objective is to set threshold values in consideration of individual differences.

To solve the problem, an aspect of the invention provides an exhaled gas detector including: a gas detection element configured to measure concentration of a specific gas; an analysis unit configured with a processor to analyze a signal output from the gas detection element; and an output unit configured to output a result analyzed by the analysis unit. The processor of the analysis unit makes the gas detection element measure the specific gas in an exhalation of non-drinking time and generate a first reference signal value for the exhalation. The processor calculates on the basis of the first reference signal value a first threshold value for determining whether a signal value from the gas detection element indicates exhalation of a person. The processor makes the gas detection element measure the specific gas in an inspection gas and generate a first measurement signal value for the inspection gas. The processor determines that the inspection gas is identified with an exhalation of a person by determining that the first measurement signal value has exceeded the first threshold value.

Other solutions will be described in the embodiments.

According to the present invention, threshold values in consideration of individual differences can be set.

DESCRIPTION OF THE PREFERRED EMBODIMENTS

Figure 1:
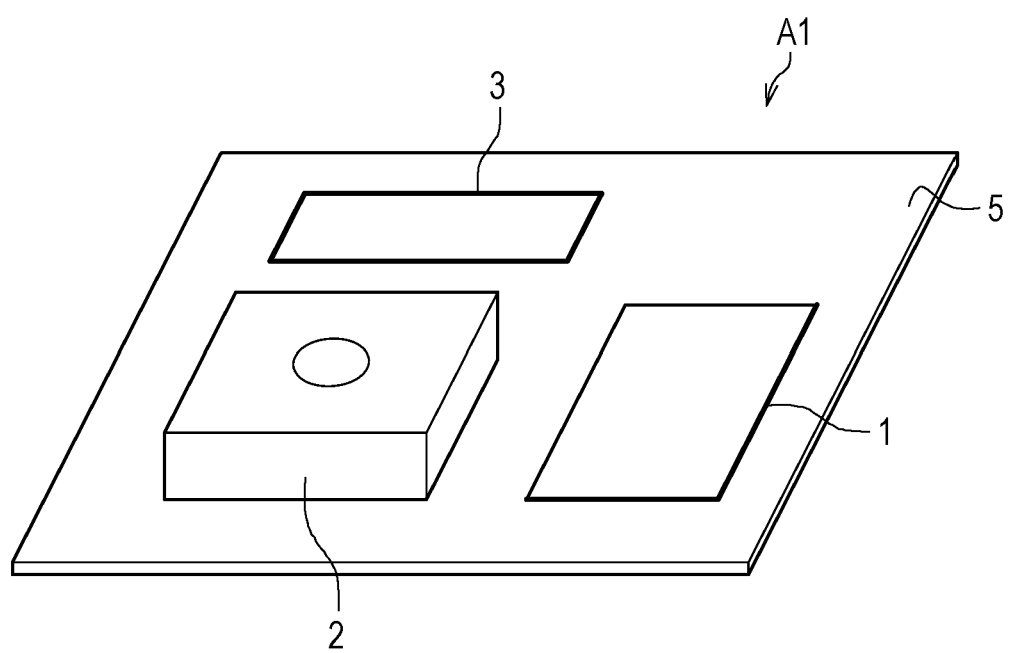
FIG. 1 is a view illustrating a schematic configuration of an exhalation detection device according to the present embodiment.

Next, modes for carrying out the present invention (referred to as "embodiments") will be described in detail with reference to the drawings as appropriate. Note that, in each of the drawings, similar constituent elements are denoted by the same reference numerals and description thereof is omitted.

First Embodiment (Device Configuration)

FIG. 1 is a view illustrating a schematic configuration of an exhalation detection device according to the present embodiment.

An exhalation detection device (referred to as an exhalation gas detector) A1 has a configuration in which a water vapor sensor (water vapor detection sensor) 1, a gas sensor (gas detection sensor) 2, and a temperature sensor (temperature detection element) 3 are installed on a substrate 5.

The water vapor sensor 1 detects whether introduced outside air is saturated water vapor. Details of the water vapor sensor 1 will be described below.

The gas sensor 2 measures a gas contained in the introduced outside air. Details of the gas sensor 2 will be described below.

The temperature sensor 3 measures the temperature of the substrate 5 (substrate temperature). Note that the temperature of the substrate 5 can be said to be substantially the same as the temperatures of the water vapor sensor 1 and the gas sensor 2.

(Water Vapor Sensor)
(Structure of Water Vapor Sensor)

Figure 2A:
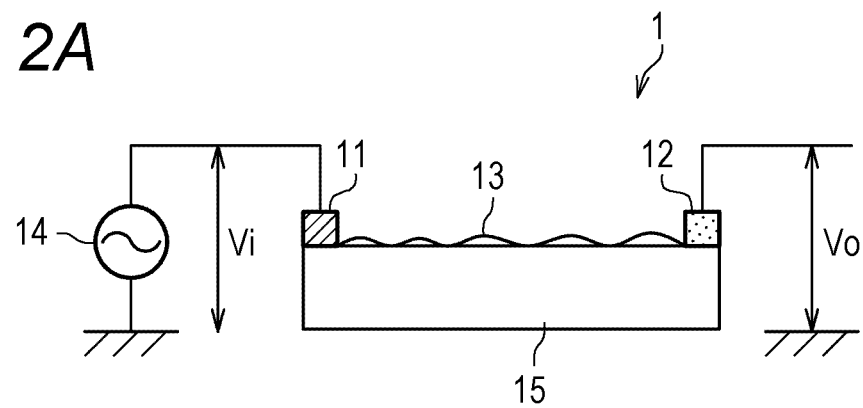
FIG. 2A is a schematic diagram illustrating a principle of a water vapor sensor.
Figure 2B:
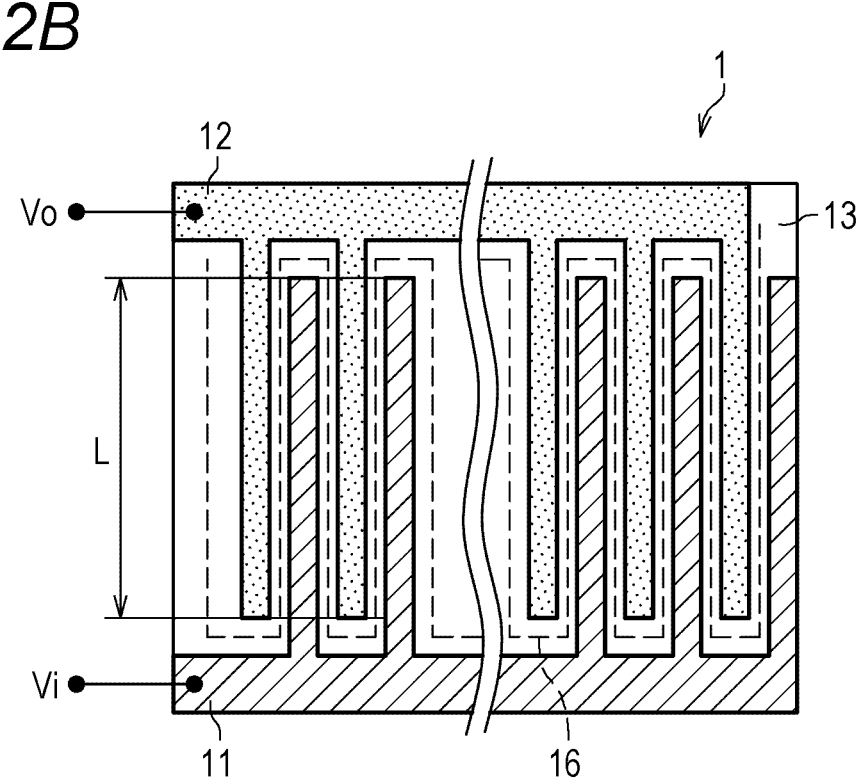
FIG. 2B is a schematic top view of the water vapor sensor.

FIGS. 2A and 2B are diagrams illustrating a structure of the water vapor sensor according to the present embodiment, and FIG. 2A is a schematic diagram illustrating a principle of the water vapor sensor. FIG. 2B is a schematic top view of the water vapor sensor.

As illustrated in FIG. 2A, the water vapor sensor 1 is connected to an alternating current power supply 14, and includes an application electrode 11 to which an application voltage Vi is applied by the alternating current power supply 14, a detection electrode 12 for detecting a potential Vo at the time of detecting water vapor, and an insulation 13.

The insulation 13 is a hydrophilic insulator provided on the substrate 15, and specifically, at least a surface is made of an oxide such as an insulating metal oxide. Note that the shape of the insulation 13 may not be substantially plate-like.

As illustrated in FIG. 2A, the insulation 13 is interposed between the detection electrode 12 and the application electrode 11. Here, the insulation 13 desirably has an uneven structure.

Further, as illustrated in FIG. 2B, a heater 16 is embedded in the substrate 15 of the water vapor sensor 1. Alternatively, the heater 16 may be provided between the substrate 15 and the insulation 13. Then, as illustrated to FIG. 2B, the heater 16 is installed to thread between the application electrode 11 and the detection electrode 12. Incidentally, the heater 16 is omitted in FIG. 2A.

(Water Vapor Detection Principle)

Figure 3A:
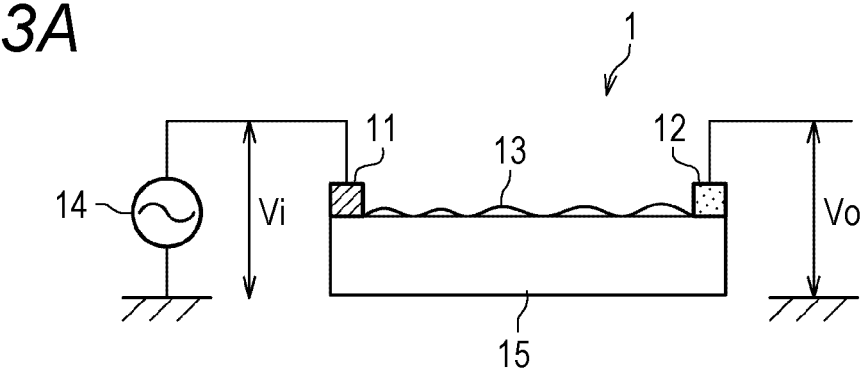
FIG. 3A is a schematic diagram illustrating a principle of the water vapor sensor before adhesion of water vapor.
Figure 3B:
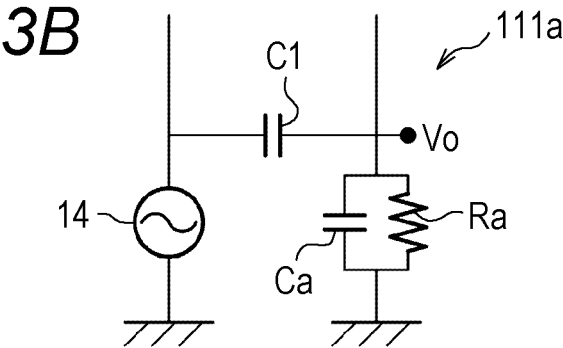
FIG. 3B is a diagram illustrating an equivalent circuit of the water vapor sensor before adhesion of water vapor.
Figure 3C:
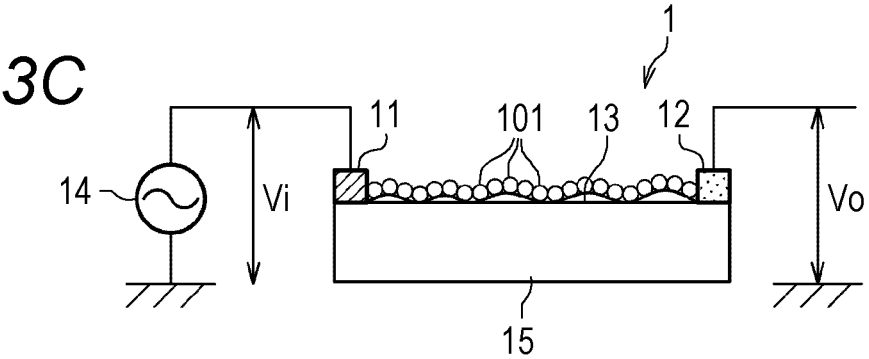
FIG. 3C is a schematic diagram illustrating a principle of the water vapor sensor after adhesion of water vapor.
Figure 3D:
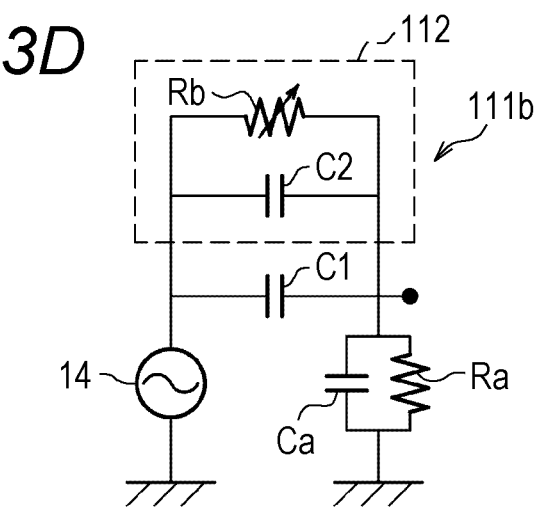
FIG. 3D is a diagram illustrating an equivalent circuit of the water vapor sensor after adhesion of water vapor.

FIGS. 3A to 3D are diagrams for describing principle of detecting water vapor by the water vapor sensor according to the present embodiment. FIG. 3A is a schematic diagram illustrating a principle of the water vapor sensor before adhesion of water vapor. FIG. 3B is a diagram illustrating an equivalent circuit of the water vapor sensor before adhesion of water vapor. FIG. 3C is a schematic diagram illustrating a principle of the water vapor sensor after adhesion of water vapor. FIG. 3D is a diagram illustrating an equivalent circuit of the water vapor sensor after adhesion of water vapor.

Note that configurations illustrated in FIGS. 3A and 3C are similar to the configuration illustrated in FIG. 2A. Therefore, the same reference numerals are denoted and description is omitted.

As illustrated in FIG. 3A, the detection electrode 12 and the application electrode 11 are connected via the insulation 13, and there is no current flow between the detection electrode 12 and the application electrode 11 before adhesion of water vapor. Therefore, although an alternating voltage is applied to the application electrode 11, no voltage is detected from the detection electrode 12.

Then, when water vapor adheres to the insulation 13 of the water vapor sensor 1, water molecules 101 adhere (condenses) to the insulation 13, as illustrated in FIG. 3C. The adhesion of the water molecules 101 allows a current to flow between the detection electrode 12 and the application electrode 11 through the water molecules 101 as a path. Then, the voltage applied from the detection electrode 12 to the application electrode 11 is detected (output). The water vapor sensor 1 detects the water vapor on the basis of the detected (output) voltage.

Next, changes in equivalent circuits 111a and 111b of the water vapor sensor 1 before and after adhesion of water vapor are compared.

Before adhesion of water vapor, the equivalent circuit 111a as illustrated in FIG. 3B is obtained. Here, a capacitor C1 is a capacitor representing the insulation 13. Since the distance between the detection electrode 12 and the application electrode 11 is sufficiently large, capacitance of the capacitor C1 is a small value (<<1). Therefore, capacitive reactance of the equivalent circuit 111a illustrated in FIG. 3B is a large value, and almost no passage of a current between the detection electrode 12 and the application electrode 11.

Incidentally, a circuit constituted by a capacitor Ca and a resistor Ra is an equivalent circuit of the atmosphere.

Here, when the water vapor contained in the exhalation adheres, the equivalent circuit 111a illustrated in FIG. 3B becomes the equivalent circuit 111b illustrated in FIG. 3D. In the equivalent circuit 111b, a circuit 112 indicated by a resistor Rb and a capacitor C2 is an equivalent circuit of the water molecules 101.

As illustrated in FIG. 3C, when the water vapor (water molecules 101) adheres to the insulation 13, the resistor Rb and the capacitor C2 resulting from the water molecules 101 are generated as illustrated in FIG. 3D. The resistor Rb and the capacitor C2 cause impedance changes (decreases). As a result, a current is allowed to flow between the detection electrode 12 and the application electrode 11, and the voltage can be detected from the detection electrode 12. As described above, the water vapor in the exhalation is detected using the change in impedance of the water vapor sensor 1 due to adhesion of the water vapor (water molecules 101) to the insulation 13, whereby responsiveness can be increased. Note that the impedance of the equivalent circuit 112 decreases as an adhesion amount of the water molecules 101 increases.

As illustrated in FIG. 2B, the detection electrode 12 and the application electrode 11 have a comb-like shape. Then, the detection electrode 12 and the application electrode 11 are installed with a space such that respective comb teeth are engaged with each other on the insulation 13. This installation makes the area of the water vapor adhesion site (reaction portion) increased.

For example, common humidity sensors are intended to measure the humidity in the air.

In contrast, the water vapor sensor 1 according to the present embodiment aims at detecting high-humidity exhalation (almost in a saturated state). Therefore, the water vapor sensor 1 according to the present embodiment does not intend to measure the water vapor amount in the air, and detection of the high-humidity air (exhalation) is sufficient.

The water vapor sensor 1 according to the present embodiment has a configuration in which the insulation 13 is interposed between the detection electrode 12 and the application electrode 11, as illustrated in FIGS. 2A and 2B. Then, as illustrated in FIG. 3C, the water molecules 101 contained in the exhalation adhere to the insulation 13 so that a current is allowed to flow through the water molecules 101 as a path. Thereby, an output voltage is detected by the detection electrode 12. Therefore, the water vapor sensor 1 according to the present embodiment can be downsized as long as the insulation 13 has an area large enough to allow the water molecules 101 to adhere thereto.

In addition, the output voltage is approximately 0 before the water vapor (water molecules 101) adhere to the insulation 13, whereas the output voltage can be approximately Vi (application voltage) after adhesion of the water vapor (water molecules 101). Thereby, an excellent a signal to noise (S/N) ratio is achieved.

In the water vapor sensor 1, the surface of the insulation 13 desirably has an uneven structure, as described above. With the uneven surface of the insulation 13, the surface area of the insulation 13 increases. That is, with the uneven surface of the insulation 13, more water molecules 101 can adhere to the surface, the output voltage increases, and high sensitivity is achieved.

Furthermore, the insulation 13 has at least the surface made of a highly hydrophilic oxide (metal oxide), thereby causing the water vapor to easily adhere to the surface.

Figure 4:
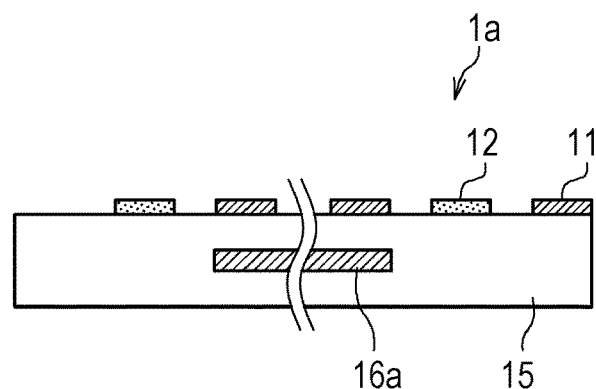
FIG. 4 is a view (part 1) illustrating another example of an installation position of a heater of the water vapor sensor according to the present embodiment.
Figure 5:
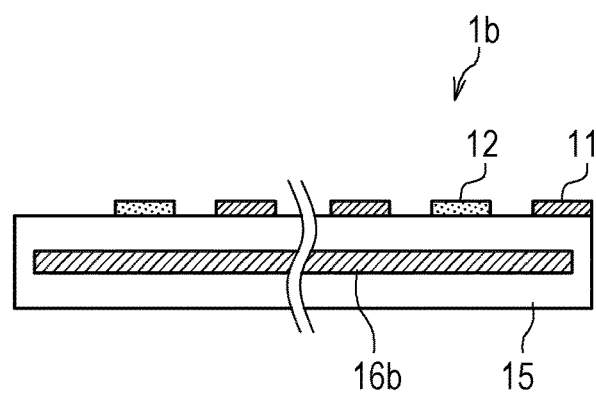
FIG. 5 is a view (part 2) illustrating another example of the installation position of the heater of the water vapor sensor according to the present embodiment.

FIGS. 4 and 5 are views illustrating other examples of an installation position of the heater of the water vapor sensor according to the present embodiment. FIGS. 4 and 5 illustrate schematic cross-sectional views of water vapor sensors 1a and 1b.

In the example illustrated in FIG. 2B, the heater 16 is installed in the substrate 15 to thread between the application electrode 11 and the detection electrode 12. Note that the configuration is not limited to the example as long as the substrate 15 of the water vapor sensor 1 can be warmed to evaporate moisture adhering to the insulation 13.

For example, as illustrated in FIG. 4, a plate-like heater 16a may be provided near the center of the substrate 15 of the water vapor sensor 1a. Alternatively, as illustrated in FIG. 5, a plate-like heater 16b may be provided substantially throughout the substrate 15 of the water vapor sensor 1b.

Note that the water vapor sensor 1 in the present embodiment has a configuration as illustrated in FIGS. 2A to 5. However, the configuration illustrated in FIGS. 2A to 5 may not be adopted as long as the presence or absence of moisture adhesion can be determined and the heater 16 that evaporates the moisture is provided.

[Gas Sensor]

Figure 6:
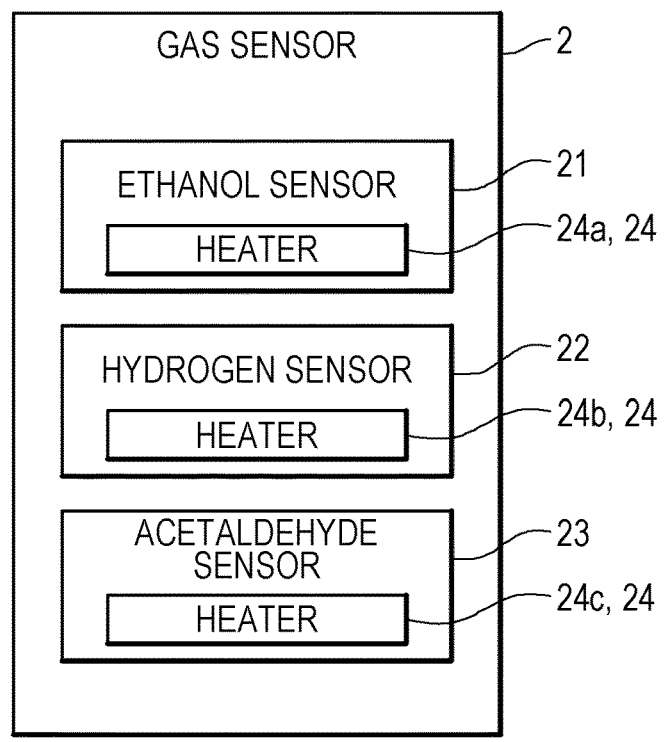
FIG. 6 is a block diagram illustrating an example of a gas sensor according to the present embodiment.

FIG. 6 is a block diagram illustrating an example of the gas sensor according to the present embodiment.

The gas sensor 2 has an ethanol sensor 21, a hydrogen sensor 22, and an acetaldehyde sensor 23. The ethanol sensor 21, the hydrogen sensor 22 and the acetaldehyde sensor 23 are respectively provided with heaters 24a to 24c (24).

As illustrated in FIG. 6, the gas sensor 2 includes the ethanol sensor 21, the hydrogen sensor 22, and the acetaldehyde sensor 23, and thus can determine drinking or non-drinking.

(System Configuration)

Figure 7:
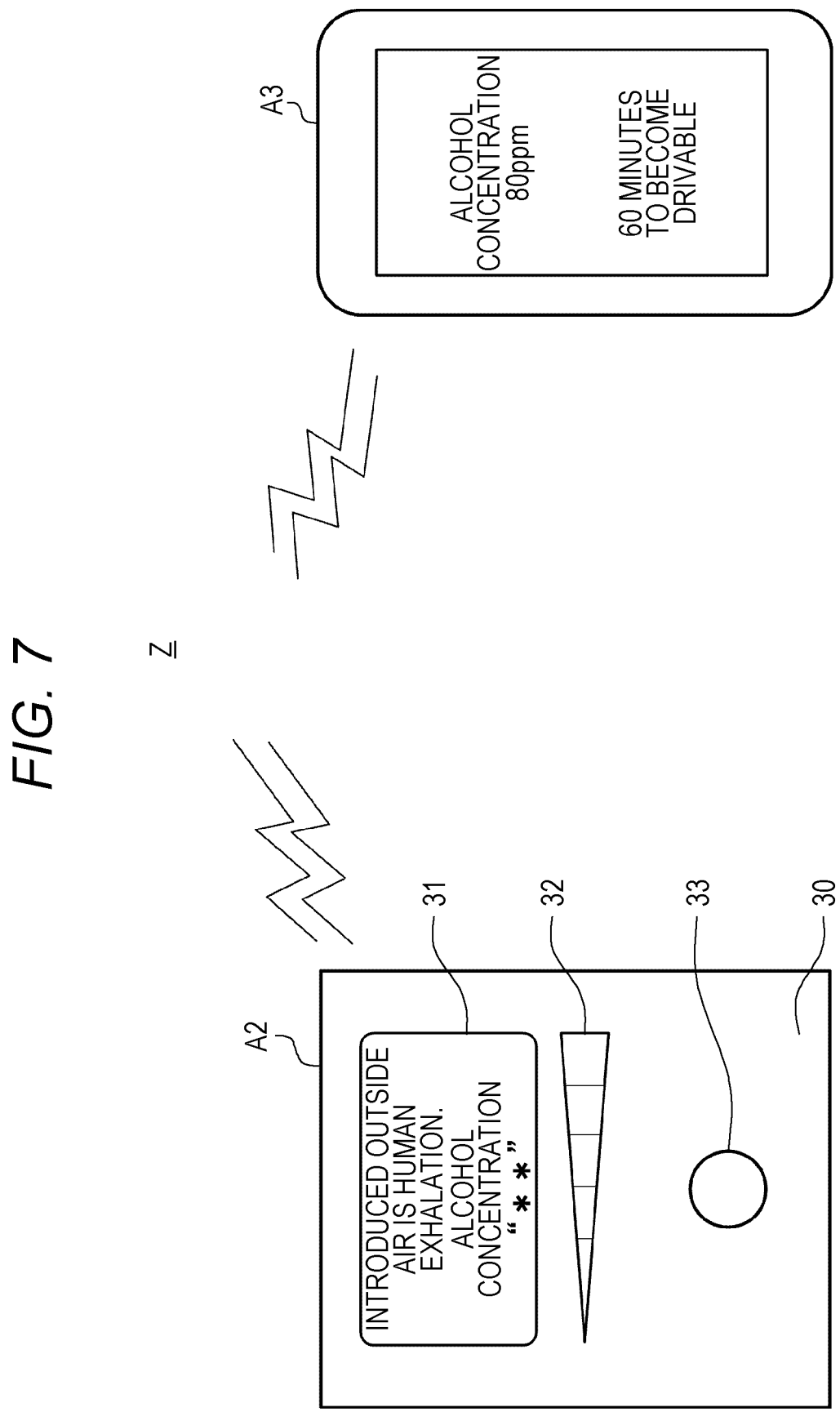
FIG. 7 is a diagram illustrating a configuration of an exhalation measurement system according to the present embodiment.

FIG. 7 is a diagram illustrating a configuration of an exhalation measurement system according to the present embodiment.

As illustrated in FIG. 7, the exhalation measurement system Z includes an exhaled gas detection device A2 and a portable device A3 such as a smartphone.

The exhaled gas detection device A2 has a size enough to be held by a person with one hand, and includes a display device (output unit) 31 provided on a housing 30, an indicator (output unit) 32, and an introduction section 33.

A user introduces exhalation (outside air) through the introduction section 33 into the exhaled gas detection device A2. With the introduction, the exhalation (outside air) is blown against the exhalation detection device A1 provided inside the exhaled gas detection device A2.

Then, the exhaled gas detection device A2 performs threshold value change processing, gas sensor initialization processing, false detection prevention processing, and the like, and then determines whether the introduced outside air (gas) is exhalation of a person, as described below. Then, the exhaled gas detection device A2 displays information such as measured gas concentration on the display device 31.

Further, the indicator 32 displays an amount of introduced exhalation (exhalation introduction amount). The indicator 32 displays peak intensity of an output voltage output from the water vapor sensor 1. Note that the gas concentration is ethanol concentration, acetaldehyde concentration, hydrogen concentration, and the like.

Then, the display device 31 displays a determination result as to whether the introduced outside air (gas) is exhalation of a person and measured alcohol concentration (ethanol concentration).

Furthermore, the exhaled gas detection device A2 calculates a drivable time that is a time for which the alcohol concentration (ethanol concentration) falls to a drivable level, and transmits the calculated drivable time and the like to the portable device A3.

The portable device A3 is a device owned by the user, and displays the transmitted information such as the drivable time. Note that the exhaled gas detection device A2 may display the drivable time and the like. Further, the exhaled gas detection device A2 may display the determination result as to whether the outside air (gas) introduced into the portable device A3 is exhalation of a person and the measured alcohol concentration (ethanol concentration).

Figure 8:
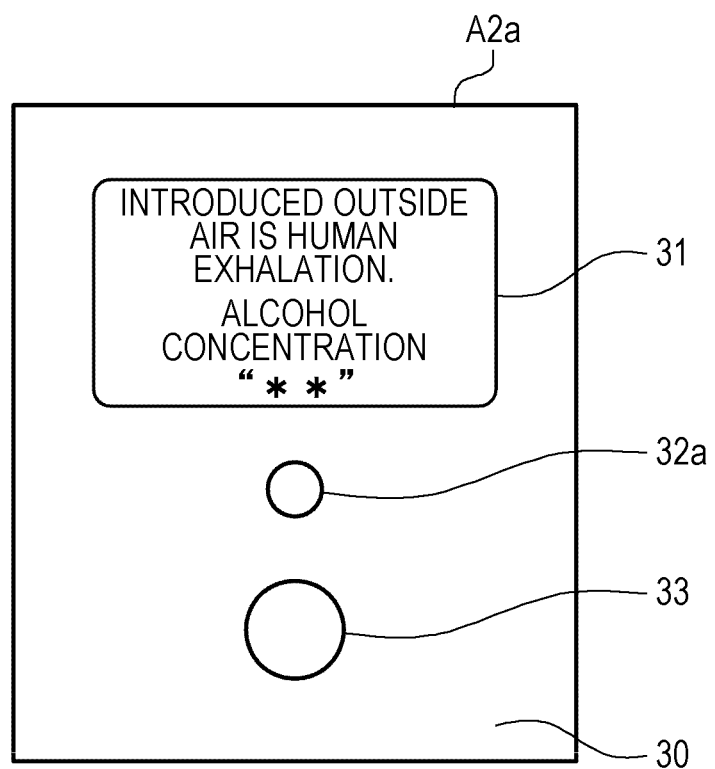
FIG. 8 is a diagram illustrating another example of the exhaled gas detection device according to the present embodiment.

FIG. 8 is a diagram illustrating another example of the exhaled gas detection device according to the present embodiment. In FIG. 8, similar configurations to FIG. 7 are denoted by the same reference numerals and description is omitted.

An exhaled gas detection device A2a illustrated in FIG. 8 is provided with a speaker (output unit) 32a instead of the indicator 32 in FIG. 7.

In the exhaled gas detection device A2a, exhalation introduction intensity (exhalation introduction amount) is indicated by change of a sound. For example, in response to a weak exhalation introduction intensity, a small sound or a low-pitched sound is emitted, and as the exhalation introduction intensity becomes stronger, the larger sound or a higher-pitched sound is emitted. Note that the exhalation introduction intensity is based on the magnitude of the output voltage of the water vapor sensor 1 and is proportional to the exhalation introduction amount. Alternatively, the exhalation introduction intensity may be exhibited with an interval of the emitted sound. That is, the interval of the emitted sound is short in response to a weak exhalation introduction intensity, and the interval of the emitted sound becomes longer as the exhalation introduction intensity becomes stronger.

In the examples illustrated in FIGS. 7 and 8, the display device 31 illustrates only the information regarding the alcohol concentration (ethanol concentration), but may illustrate detailed information such as the hydrogen concentration and acetaldehyde concentration.

The exhalation introduction amount is exhibited with the display or sounds on the exhaled gas detection device A2 or A2a in this way, whereby the usability is improved. In addition, the user can confirm whether the exhalation necessary for alcohol (ethanol) detection has been introduced into the exhaled gas detection device A2 or A2a.

[Outline of Processing of Present Embodiment]

Figure 9:
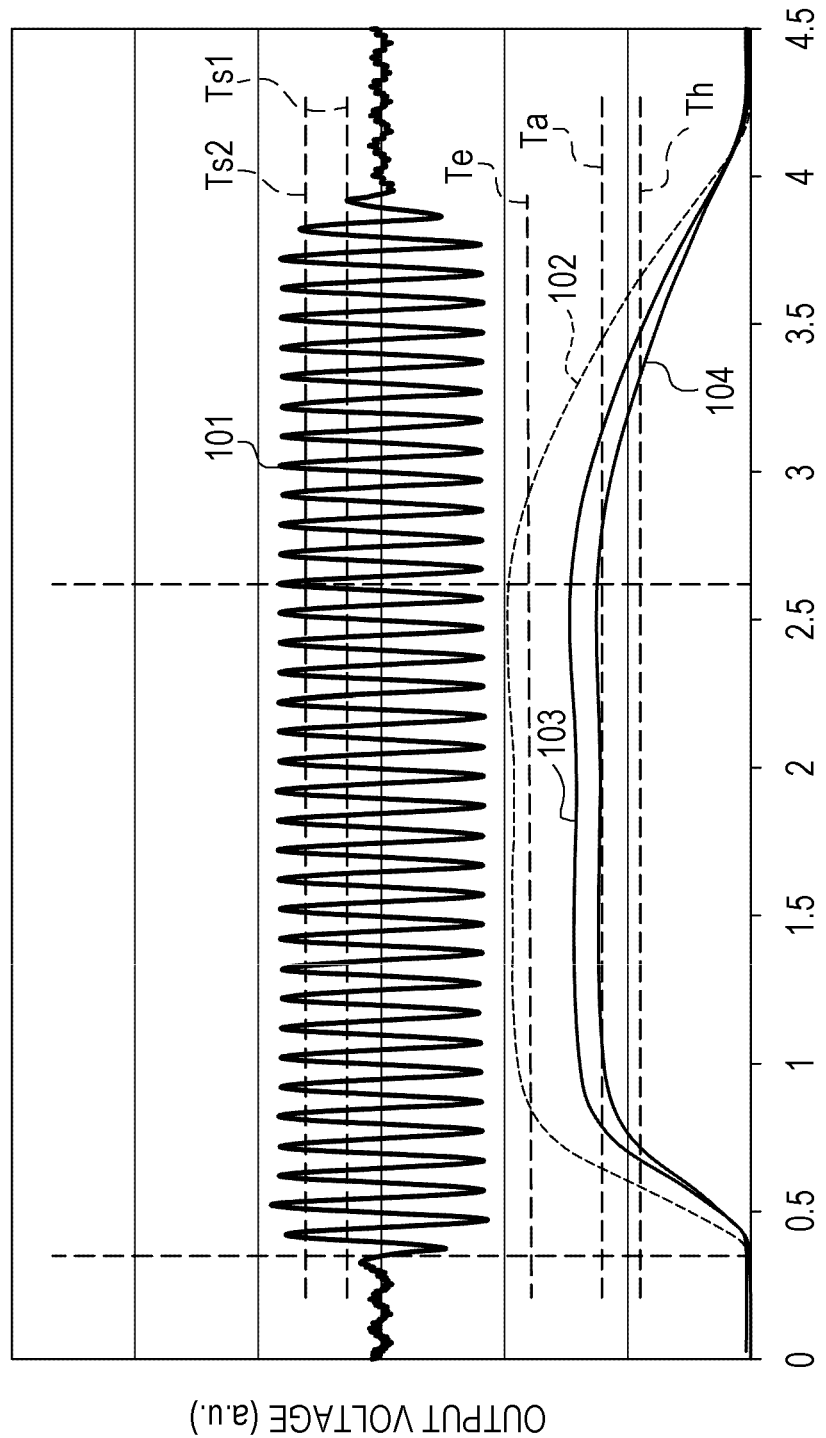
FIG. 9 is a graph for describing an outline of processing in the present embodiment.

FIG. 9 is a graph for describing an outline of processing in the present embodiment. FIGS. 2A and 2B and FIG. 6 will be referred to, as appropriate.

In FIG. 9, the horizontal axis represents time and the vertical axis represents the output voltage (arbitrary unit). Here, the output voltage is outputs of the water vapor sensor 1, the ethanol sensor 21, the hydrogen sensor 22, and the acetaldehyde sensor 23. Note that the output of the water vapor sensor 1 is a pulsating flow or an alternating current.

A waveform 101 indicates the output voltage of the water vapor sensor 1. As described above, since the alternating voltage is applied to the water vapor sensor 1, the output voltage becomes an alternating waveform.

Two threshold values Ts1 (fourth threshold value) and Ts2 are set in the output voltage of the water vapor sensor 1. Between the two threshold values, the threshold value Ts1 is a threshold value used in condensation avoidance processing described below, and is a threshold value for determining whether moisture adheres to the insulation 13 of the water vapor sensor 1 due to condensation or the like although exhalation has not been introduced. Further, the threshold value Ts2 is a threshold for determining whether the exhalation has been sufficiently introduced into the exhaled gas detection device A2.

A waveform 102 indicates the output voltage of the ethanol sensor 21, a waveform 103 indicates the output voltage of the acetaldehyde sensor 23, and a waveform 104 indicates the output voltage of the hydrogen sensor 22.

Then, threshold values Te, Ta, and Th (first threshold value) are set for the respective output voltages of these gas sensors 2. That is, the threshold value Te is a threshold value for the output voltage of the ethanol sensor 21. Further, the threshold value Ta is a threshold value for the output voltage of the acetaldehyde sensor 23. Then, the threshold value Th is a threshold value for the output voltage of the hydrogen sensor 22.

These threshold values Te, Ta, and Th are threshold values for determining whether the outside air introduced to the exhaled gas detection device A2 is exhalation of a person.

The exhalation of a person contains alcohol (ethanol), acetaldehyde, and hydrogen in trace amounts even if the person has not been drinking. The threshold values Te, Ta, and Th are set low enough to detect the output voltages of the ethanol sensor 21, the acetaldehyde sensor 23, and the hydrogen sensor 22 at the time of non-drinking.

The threshold values Te, Ta, and Th for the output voltages of the gas sensors 2 are set in this manner, whereby the exhalation can be distinguished from the outside air that only contains water vapor, and impersonation can be prevented.

(Exhalation Measurement Device Block Diagram)

Figure 10:
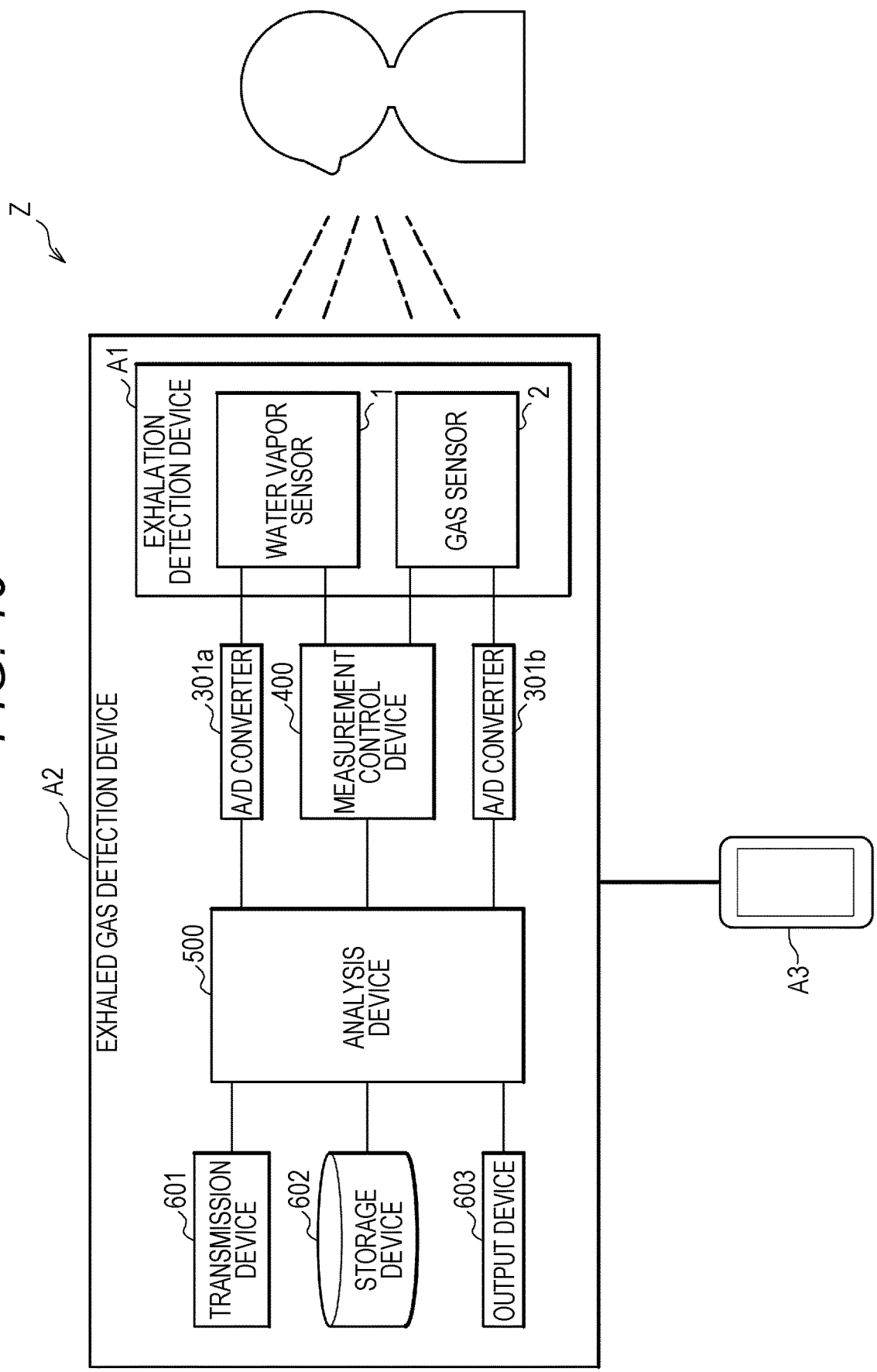
FIG. 10 is a diagram illustrating an example of functional blocks of the exhaled gas detection device according to the present embodiment.

FIG. 10 is a diagram illustrating an example of functional blocks of the exhaled gas detection device according to the present embodiment.

The exhalation measurement system Z includes the exhaled gas detection device A2, and the portable device A3 such as a smartphone capable of communicating with the exhaled gas detection device A2. The exhaled gas detection device A2 and the portable device A3 are favorably connected by a wire (for example, a USB cable) including power supply to the exhaled gas detection device A2. However, in a case where the power supply of the exhaled gas detection device A2 is separately available, wireless communication as illustrated in FIG. 7 may be adopted. The exhaled gas detection device A2 includes the exhalation detection device A1, analog/digital (A/D) converters 301a and 301b, a measurement control device 400, and an analysis device (analysis unit) 500. In addition, the exhaled gas detection device A2 includes a transmission device 601, a storage device 602, and an output device 603. The exhalation detection device A1, the analog/digital (A/D) converters 301a and 301b, the measurement control device 400, the analysis device 500, the transmission device 601, and the storage device 602 are all provided in the housing 30 (see FIGS. 7 and 8).

The exhalation detection device A1 includes the water vapor sensor 1 and the gas sensor 2. These sensors have been described above with reference to FIGS. 1 to 9 and thus description thereof is omitted here.

The measurement control device 400 converts a frequency of the alternating current power supply 14 (see FIG. 2A) and outputs the converted frequency.

Further, the exhalation detection device A1 converts analog signals input from the water vapor sensor 1 and the gas sensor 2 into digital signals in the analog/digital (A/D) converters 301a and 301b, and outputs the digital signals to the analysis device 500.

The analysis device 500 acquires the output voltage from the water vapor sensor 1 in the exhalation detection device A1, and acquires the output voltage from the gas sensor 2. Then, the analysis device 500 determines whether the introduced outside air (gas) is exhalation of a person and analyzes the gas content in the exhalation on the basis of the output voltage acquired from the water vapor sensor 1 and the output voltage acquired from the gas sensor 2. Note that, in the present embodiment, the analysis device 500 acquires the output voltages from the exhalation detection device A1. However, the present invention is not limited thereto, and the measurement control device 400 may acquire the output voltages from the exhalation detection device A1 and may pass the acquired output voltages to the analysis device 500.

The storage device 602 stores the output voltage acquired from the water vapor sensor 1 and the output voltage acquired from the gas sensor 2 by the analysis device 500 together with an inspection time, and stores an analysis result by the analysis device 500.

The transmission device 601 transmits the analysis result and the like by the analysis device 500 to the portable device A3.

The output device 603 is the display device 31 or the indicator 32 in FIG. 7 or the speaker 32a or the like in FIG. 8.

The analysis result by the analysis device 500 is passed to the portable device A3. The portable device A3 stores the passed analysis result in a storage device (not illustrated) and displays information regarding the analysis result on a display device (not illustrated). Note that the portable device A3 can be omitted.

(Measurement Control Device)

Figure 11:
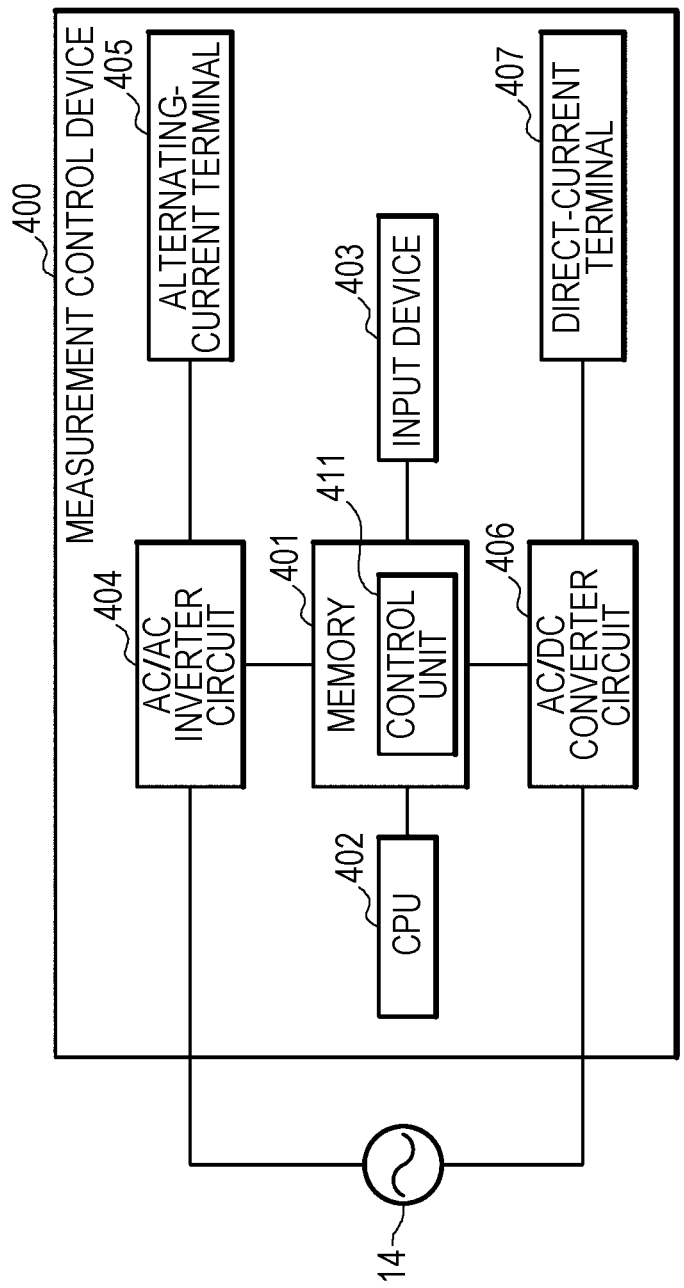
FIG. 11 is a functional block diagram illustrating a configuration example of a measurement control device according to the present embodiment.

FIG. 11 is a functional block diagram illustrating a configuration example of a measurement control device according to the present embodiment.

The measurement control device 400 includes a memory 401, a central processing unit (CPU) 402, an input device 403, an AC/AC inverter circuit 404, an alternating current terminal 405, an AC/DC converter circuit 406, and a direct current terminal 407.

A control unit 411 is embodied in the memory 401 by the CPU 402 executing a program.

The control unit 411 sends an instruction to the AC/AC inverter circuit 404 or the like on the basis of information input through the input device 403.

The input device 403 is a button or the like (not illustrated) provided on the housing 30 (see FIGS. 7 and 8) of the exhaled gas detection device A2. The user operates the input device 403 to adjust the frequency and voltage of the alternating voltage output from the alternating current terminal 405. Thus, adjusting the frequency and voltage of the alternating voltage output from the alternating current terminal 405 makes it possible to adjust the frequency and the output voltage of the water vapor sensor 1 connected to the alternating current terminal 405. For example, if the output of the water vapor sensor 1 is low no matter how much exhalation is introduced, the voltage output from the alternating current terminal 405 can be increased. If the frequency of the waveform of the output voltage of the water vapor sensor 1 is low and calculation of a peak frequency ratio RB described below is difficult, the frequency can be adjusted to be high.

The AC/AC inverter circuit 404 converts the frequency and voltage of the alternating voltage input from the alternating current power supply 14 on the basis of the instruction sent from the control unit 411, and outputs the converted data to the alternating current terminal 405. The water vapor sensor 1 is connected to the alternating current terminal 405.

Further, the AC/DC converter circuit 406 converts the voltage of the alternating voltage input from the alternating current power supply 14 and further converts an alternating current into a direct current on the basis of the instruction sent from the control unit 411, and outputs the converted data to the direct current terminal 407. The gas sensor 2 is connected to the direct current terminal 407.

Note that the configuration of the measurement control device 400 illustrated in FIG. 11 is an example, and the embodiment is not limited to the configuration illustrated in FIG. 11. For example, an alternating current signal (alternating voltage) may be generated using a crystal oscillator.

(Analysis Device)

Figure 12:
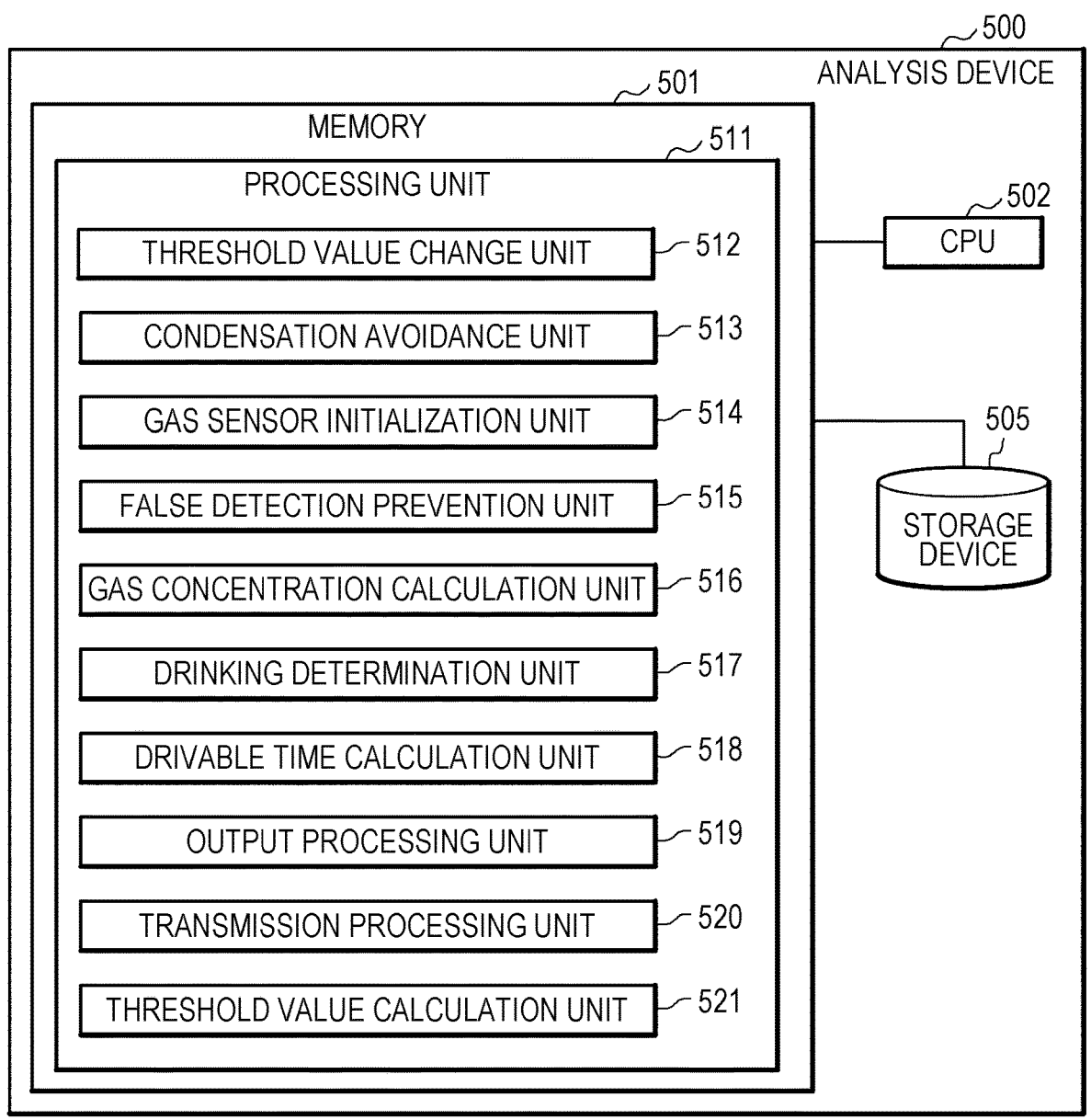
FIG. 12 is a functional block diagram illustrating a configuration example of an analysis device according to the present embodiment.

FIG. 12 is a functional block diagram illustrating a configuration example of the analysis device according to the present embodiment.

The analysis device 500 includes a memory 501, a CPU 502, a storage device 505, and the like.

A program stored in the storage device 505 is loaded into the memory 501, and this program is executed by the CPU 502. With the execution of the program, a processing unit 511, and a threshold value change unit 512, a condensation avoidance unit 513, a gas sensor initialization unit 514, a false detection prevention unit 515, a gas concentration calculation unit 516, a drinking determination unit 517, a drivable time calculation unit 518, an output processing unit 519, a transmission processing unit 520, and a threshold value calculation unit (analysis unit) 521 constituting the processing unit 511 are embodied.

The threshold value change unit 512 changes the threshold value Ts2 in accordance with substrate temperature of the water vapor sensor 1.

After the exhaled gas detection device A2 is powered on, the condensation avoidance unit 513 determines whether there is passage of a current due to condensation or the like. Then, in a case where there is the passage of a current due to condensation or the like, the condensation avoidance unit 513 turns on the heater 16 provided in the water vapor sensor 1 to warm the substrate 15 (see FIG. 2) to evaporate the moisture originating from the condensation or the like.

Although the water vapor sensor 1 is heated by the heater 16, the temperature of the water vapor sensor 1 is lowered by introduction of a large amount of exhalation, so the influence of heating by the heater 16 may not be taken into consideration.

The gas sensor initialization unit 514 determines whether there is passage of a current in the gas sensor 2 due to adhesion of a gas or the like after the exhaled gas detection device A2 is powered on. Then, if there is the passage of a current due to adhesion of a gas or the like, the gas sensor initialization unit 514 turns on the heater 24 provided in the gas sensor 2 to remove the gas.

Note that the ethanol sensor 21, the hydrogen sensor 22, and the acetaldehyde sensor 23 constituting the gas sensor 2 are heated by the heaters 24a to 24c. Note that the influence of heat may not be taken into consideration in a case of a catalytic combustion sensor, a new ceramic sensor, or a thermal particle sensor.

The false detection prevention unit 515 determines whether the output voltages obtained from both the water vapor sensor 1 and the gas sensor 2 have exceeded the threshold values. With the determination, it is determined whether the outside air (gas) introduced to the exhaled gas detection device A2 is exhalation of a person.

The gas concentration calculation unit 516 calculates the concentration of the gas (such as ethanol) contained in the outside air introduced into the exhaled gas detection device A2 on the basis of the output voltage of the gas sensor 2.

The drinking determination unit 517 determines whether the user has been drinking on the basis of the concentration of the gas contained in the outside air calculated by the gas concentration calculation unit 516.

The drivable time calculation unit 518 calculates the drivable time that is a time for which the alcohol concentration (ethanol concentration) falls to a drivable level on the basis of the gas concentration in the outside air calculated by the gas concentration calculation unit 516.

The output processing unit 519 has the output device 603 (see FIG. 10) or the like output information.

The transmission processing unit 520 transmits information to the portable device A3 via the transmission device 601 (see FIG. 10).

The threshold value calculation unit 521 calculates, sets, or updates threshold values TG and Tw described below on the basis of the exhalation introduced a plurality of times (three times in the present embodiment). The threshold values TG and Tw will be described below.

Note that the threshold value change unit 512 to the threshold value calculation unit 521 may be mounted on the portable device A3 as needed.

Note that, in FIG. 10, the exhalation detection device A1, the A/D converters 301a and 301b, the measurement control device 400, the analysis device 500, the transmission device 601, and the storage device 602 are provided in the one exhaled gas detection device A2. However, an embodiment is not limited to the configuration. For example, the exhalation detection device A1, the A/D converters 301a and 301b, and the measurement control device 400 may be provided in the exhaled gas detection device A2, and the analysis device 500, the transmission device 601, and the storage device 602 may be provided in a server installed in an analysis center, or the like.

(Flowchart)
(Overall Flowchart)

Figure 13:
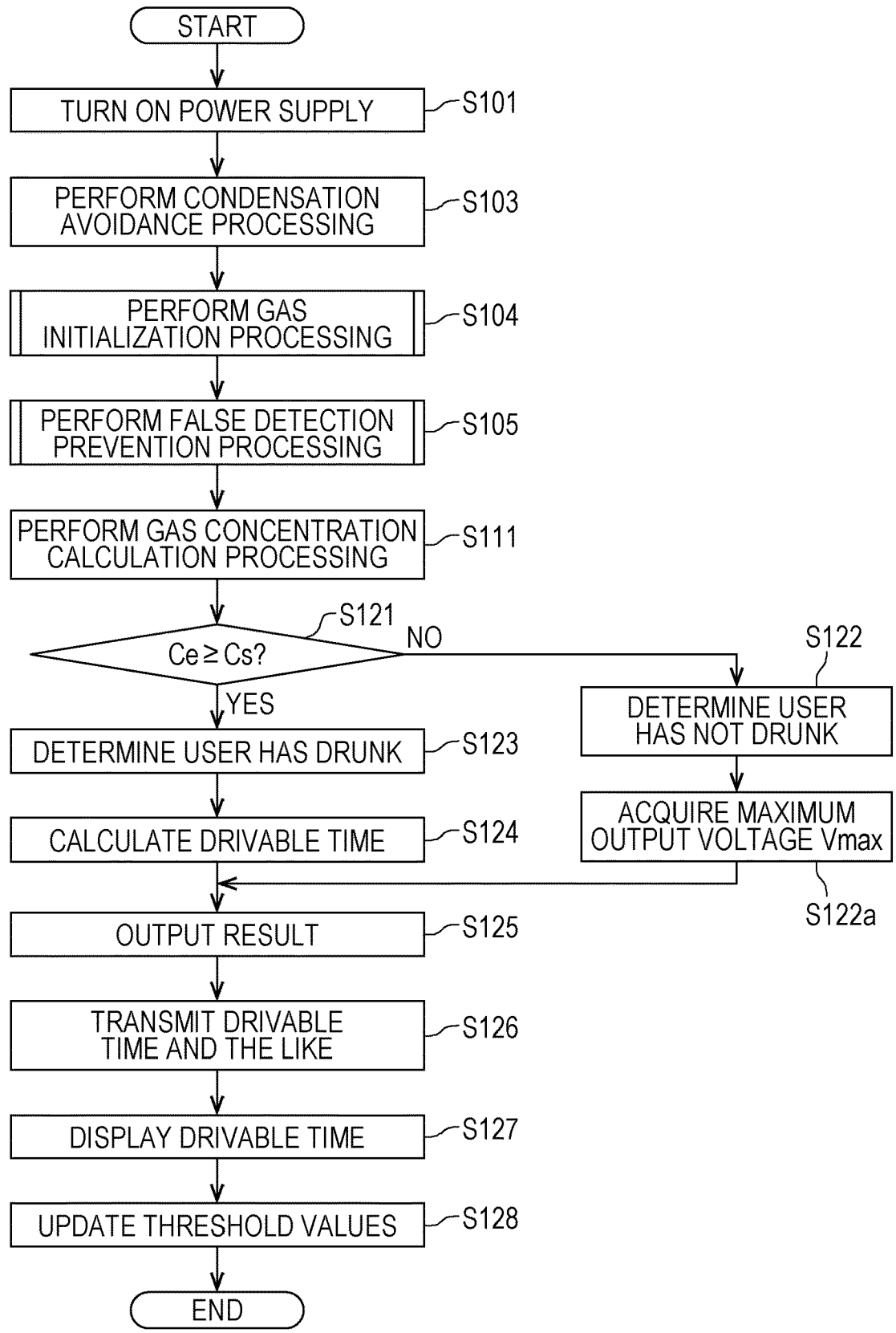
FIG. 13 is a flowchart illustrating a processing procedure of the exhalation measurement system according to the present embodiment.

FIG. 13 is a flowchart illustrating a processing procedure of the exhalation measurement system according to the present embodiment. In the following description, FIGS. 1, 6 to 8, 10, and 12 will be referred to, as appropriate.

First, the exhaled gas detection device A2 is powered on (S101).

Next, the condensation avoidance unit 513 performs the condensation avoidance processing (S103). Here, it is determined whether a present output voltage Vs of the water vapor sensor 1 is equal to or larger than a threshold value Ts1 before introduction of the outside air (exhalation). With the determination, the exhaled gas detection device A2 can prevent false detection due to adhesion of the moisture originating from the condensation or the like to the water vapor sensor 1. Further, in if the present output voltage Vs of the water vapor sensor 1 is equal to or larger than the threshold value Ts1 before introduction of the outside air (exhalation), the heater 16 is kept ON for a predetermined time. The heating makes it possible for the exhaled gas detection device A2 to evaporate the moisture adhering to the water vapor sensor 1 due to condensation or the like. The evaporation of the moisture prevents malfunction due to condensation.

Then, the gas sensor initialization unit 514 performs the gas sensor initialization processing (S104). The gas sensor initialization processing will be described below.

Note that the processing in steps S103 to S104 may not be performed in this order.

Next, the false detection prevention unit 515 performs the false detection prevention processing (S105). In this false detection prevention processing, it is determined whether the outside air introduced into the exhaled gas detection device A2 is exhalation of a person. The false detection prevention processing will be described below.

Then, the gas concentration calculation unit 516 performs gas concentration calculation processing for calculating the gas concentration in the introduced outside air on the basis of the output voltages acquired from the gas sensor 2 (the ethanol sensor 21, the acetaldehyde sensor 23, and the hydrogen sensor 22) in the outside air (exhalation) introduced during the processing in step S105 (S111). Here, as described above, the gas concentration is the ethanol concentration, the acetaldehyde concentration, and the hydrogen concentration. For example, the gas concentration calculation unit 516 calculates the gas concentration in an equilibrium state on the basis of known calibration curves indicating relationships between the gas concentration of the gases (ethanol, acetaldehyde, and hydrogen) and the output voltages of the gas sensor 2, and the present gas concentration. The method of calculating the gas concentration is not limited to this method.

Then, the drinking determination unit 517 determines whether ethanol concentration Ce calculated in step S111 is equal to or larger than a reference value Cs (Ce≥Cs) (S121). The value of the reference value Cs is, for example, 40 ppm including suspected drinking. The reference value Cs can be arbitrarily determined by the user on the basis of a safety standard of a country or an automobile maker. Therefore, a reference value other than the reference value Cs based on the ethanol concentration may be added to the determination in step S121.

As a result of step S121, if the ethanol concentration is less than the reference value Cs (S121→No), the drinking determination unit 517 determines that the user has not been drinking (S122).

Then, the threshold value calculation unit 521 acquires maximum output voltages V max of the gas sensor 2 and the water vapor sensor 1 obtained at this time (S122a), and stores the maximum output voltages V max in the storage device 505.

Thereafter, the processing unit 511 advances the processing to step S125.

As a result of step S121, if the ethanol concentration is equal to or larger than the reference value Cs (S121→Yes), the drinking determination unit 517 determines that the user has been drinking (S123).

Then, the drivable time calculation unit 518 calculates the drivable time on the basis of the gas concentration calculated in step S111 (S124) and advances the processing to step S125. Here, as described above, the drivable time is a time for which the ethanol concentration (alcohol concentration) falls to a drivable level. The drivable time calculation unit 518 calculates the operable time on the basis of an ethanol concentration decrease curve and the like stored in the storage device 505.

In step S125, the output processing unit 519 has the output device 603 output a result of step S121, information of the drivable time, and the like. Here, if it is determined that the user has been drinking, the output device 603 displays the fact that the user has been drinking on the display device 31, sounds a buzzer from the speaker 32*a*, or gives notice with sounds. Moreover, the output device 603 may blink a light or may light a red light in an LED light (not illustrated). Further, the output processing unit 519 may not output anything in a case where it is determined that the user has not been drinking. Note that the output processing unit 519 may notify that the user has not been drinking with sounds, or may give notice of the determination that the user has not been drinking by lighting a green light in an LED light (not illustrated) or the like.

Further, the transmission processing unit 520 transmits the drivable time and the like to the portable device A3 of the user via a transmission/reception device (S126), and the portable device A3 displays the drivable time on the display unit (S127). The drivable time is calculated and is displayed on the portable device A3 in this way, whereby the user can easily confirm how long the user will take to be drivable.

Thereafter, the threshold value calculation unit 521 updates the threshold value TG and the threshold value Tw on the basis of the maximum output voltage V max of the gas sensor 2 acquired in step S122*a* (S128). This processing will be described below. Here, the threshold value TG includes a threshold value Te1 of the ethanol sensor 21, a threshold value Th1 of the hydrogen sensor 22, and a threshold value Ta1 of the acetaldehyde sensor 23. The respective threshold values Te1, Th1, and Ta1 will be described below. The threshold value Tw includes the threshold value Te of the ethanol sensor 21, the threshold value Th of the hydrogen sensor 22, the threshold value Ta of the acetaldehyde sensor 23, and a threshold value Ts2 of the water vapor sensor 1. The respective threshold values Te, Th and Ta will be described below. The threshold value Ts2 of the water vapor sensor 1 has been described above.

(Gas Sensor Initialization Processing)

Figure 14:
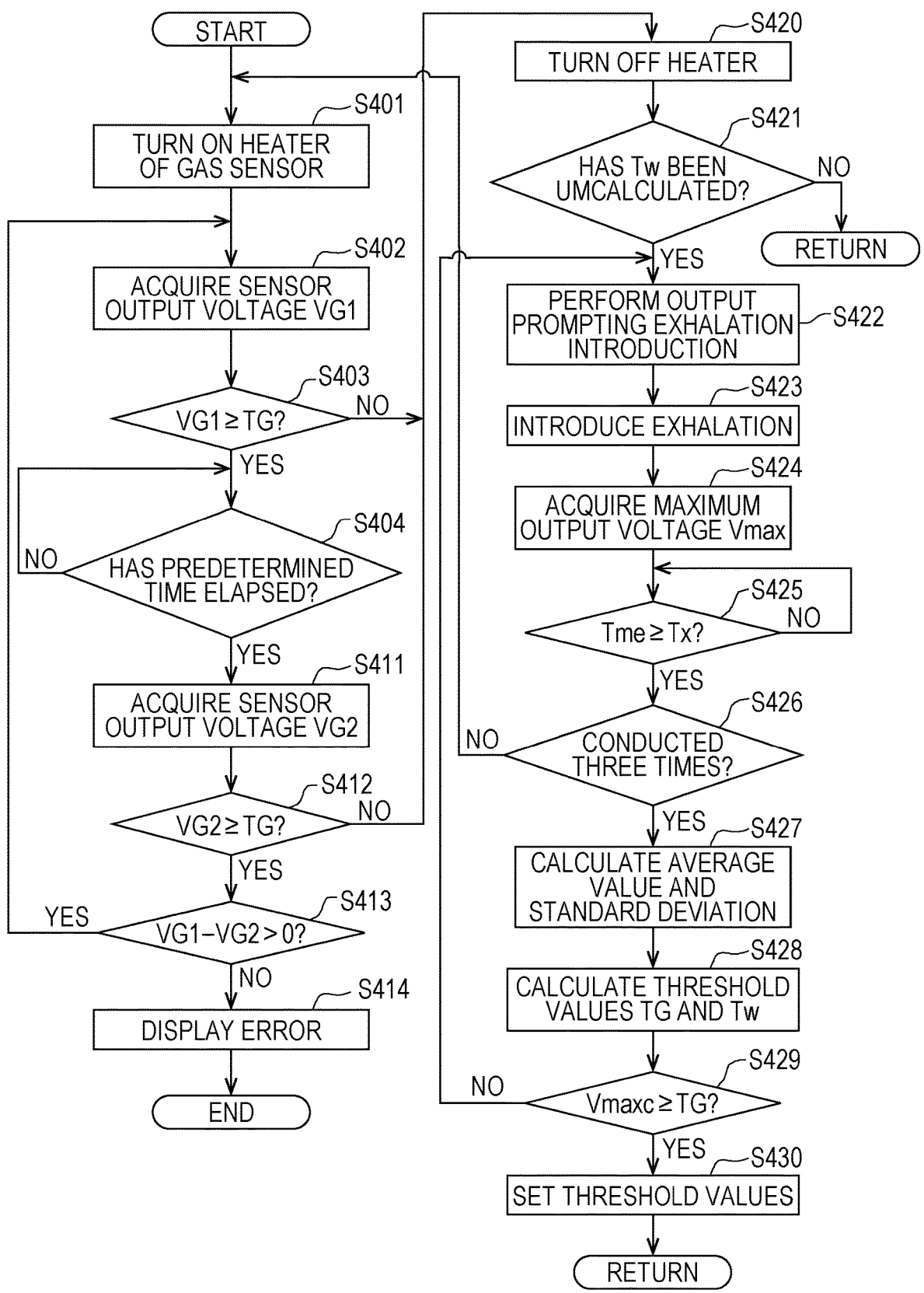
FIG. 14 is a flowchart illustrating a detailed processing procedure of gas sensor initialization processing according to the present embodiment.

FIG. 14 is a flowchart illustrating a detailed processing procedure of gas sensor initialization processing (S104 in FIG. 13) according to the present embodiment.

First, the gas sensor initialization unit 514 turns on the heater 24 (see FIG. 6) provided in the gas sensor 2 (S401).

The gas sensor initialization unit 514 acquires a present output voltage (sensor output voltage) VG1 from the gas sensor 2 (S402). The output voltage VG1 here includes the output voltage of the ethanol sensor 21, the output voltage of the acetaldehyde sensor 23, and the output voltage of the hydrogen sensor 22.

Next, the gas sensor initialization unit 514 determines whether the output voltage VG1 acquired in step S402 is equal to or larger than a predetermined threshold value TG (second threshold value) (VG1≥TG) (S403). Here, the output voltage VG1 of the gas sensor 2 being equal to or larger than the threshold value TG means that the output voltage of the ethanol sensor 21 is equal to or larger than the threshold value Te1, the output voltage of the acetaldehyde sensor 23 is equal to or larger than the threshold value Ta1, and the output voltage of the hydrogen sensor 22 is equal to or larger than the threshold value Th1. Note that these threshold values Te1, Ta1, and Th1 are the threshold values that can determine whether the gas is attached to the gas sensors 2 and are lower values than the threshold values Te, Ta, and Th illustrated in FIG. 9.

Note that, if the processing in step S403 is performed before processing of calculating the threshold value TG (S428) described below is performed, values (initially set values) preset at the time of shipment are used as the threshold value TG. The initial setting value are (but not limited to) Te1=0.4 V, Ta1=0.3 V, and Th1=0.24 V, for example.

As a result of step S403, if the output voltage VG1 is less than the predetermined threshold value TG (S403→No), the processing unit 511 advances the processing to step S421.

Incidentally, in the processing in step S403, the gas sensor initialization unit 514 determines whether the gas adheres to the gas sensor 2 according to the same logic as the determination as to whether the introduced outside air is exhalation of a person in step S522 in FIG. 17 described below.

Determination of "No" in step S403 means that the gas does not adhere to the gas sensor 2, and thus the processing unit 511 advances the processing to step S421 and moves onto calculation and setting of the threshold values TG and Tw.

As a result of step S403, in a case where the output voltage VG1 is equal to or larger than the predetermined threshold value TG (S403→Yes), the gas sensor initialization unit 514 determines whether a predetermined time has elapsed (S404). The predetermined time is (but not limited to) one minute, for example. By waiting for a predetermined time as described above, warm up of the gas sensor 2 by the heater 24 is waited.

As a result of step S404, if the predetermined time has not elapsed (S404→No), the gas sensor initialization unit 514 returns the processing to step S404.

As a result of step S404, if the predetermined time has elapsed (S404→Yes), the gas sensor initialization unit 514 acquires a present output voltage (sensor output voltage) VG2 from the gas sensor 2 (S411).

Next, the gas sensor initialization unit 514 determines whether the output voltage VG2 acquired in step S411 is equal to or larger than the predetermined threshold value TG (VG2≥TG) (S412). Here, the output voltage VG2 of the gas sensor 2 being equal to or larger than the threshold value TG means that, same as the above description, the output voltage of the ethanol sensor 21 is equal to or larger than the threshold value Te1, the output voltage of the acetaldehyde sensor 23 is equal to or larger than the threshold value Ta1, and the output voltage of the hydrogen sensor 22 is equal to or larger than the threshold value Th1.

Note that, if the processing in step S412 is performed before processing of calculating the threshold value TG (S428) described below is performed, values (initially set values) preset at the time of shipment are used as the threshold value TG. The initial setting value are (but not limited to) Te1=0.4 V, Ta1=0.3 V, and Th1=0.24 V, for example.

As a result of step S412, if the output voltage VG2 is equal to or larger than the predetermined threshold value TG (S412→Yes), the gas sensor initialization unit 514 determines whether the value of VG1−VG2 is larger than 0 (VG1−VG2>0) (S413).

As a result of step S413, if the value of VG1−VG2 is equal to or less than 0 (S413→No), the gas sensor initialization unit 514 determines that the output voltage of the gas sensor 2 is unchanged or the output voltage is rising although the heater 24 is ON. In this case, the gas sensor initialization unit 514 determines that there is a possibility that the gas sensor 2 is broken.

Then, the output processing unit 519 has the display device 31 display an error giving notice of the possibility that the gas sensor 2 is broken (S414) and terminates the processing.

As a result of step S413, if the value of VG1−VG2 is larger than 0 (S413→Yes), the output voltage of the gas sensor 2 is smoothly falling, the gas sensor initialization unit 514 returns the processing to step S402.

If "No" is determined in step S403 or "No" in step S412 (S403→No or S412→No), the gas sensor initialization unit 514 determines that the attached gas has evaporated.

Thereafter, the gas sensor initialization unit 514 turns the heater 24 off.

Then, the threshold value calculation unit 521 determines whether the threshold value Tw has not been calculated at present (uncalculated) (S421).

As a result of step S421, if the threshold value Tw has been calculated (S421→No), the processing unit 511 returns the processing to step S105 in FIG. 13.

As a result of step S421, if the threshold value Tw has not been calculated (S421→Yes), the output processing unit 519 outputs an output prompting the user to introduce exhalation via the output device 603 (display device 31) (S422). Thereafter, the outside air (exhalation) is introduced through the introduction section 33 (S423). Note that the exhalation introduced at this time is exhalation of a non-drinking time.

Then, the threshold value calculation unit 521 acquires the maximum output voltages V max of the gas sensor 2 and the water vapor sensor 1 (S424). The maximum output voltage V max refers to an amount of increase (maximum increase) before and after the exhalation.

Thereafter, the threshold value calculation unit 521 determines whether a measurement time has passed a predetermined time. (Elapsed time Tme≥Tx; S425).

As a result of step S425, if the measurement time has not exceeded the predetermined time (S425→No), the threshold value calculation unit 521 returns the processing to step S425.

As a result of step S425, if the measurement time has exceeded the predetermined time (S425→Yes), the threshold value calculation unit 521 determines whether the introduction of exhalation has been performed three times (S426).

As a result of step S426, if the introduction of exhalation has not been performed three times (S426→No), the threshold value calculation unit 521 returns the processing to step S401.

As a result of step S426, if the introduction of exhalation has been performed three times (S426→Yes), the threshold value calculation unit 521 calculates an average value and a standard deviation of the maximum output voltages V max of the gas sensor 2 and the water vapor sensor 1 (S427).

Then, the threshold value calculation unit 521 calculates the threshold value TG and the threshold value Tw by calculating the following expressions (11) and (12) (S428).

$$TG = AVE - 3\sigma \qquad (11)$$

$$Tw = AVE - \sigma \qquad (12)$$

A calculation method to be described in a second embodiment may be used as the threshold value TG.

Further, although in the expressions (11) and (12), −3σ and −σ are used, other coefficients such as −2σ or +σ and calculation expressions may be used depending on the situation.

In the expressions (11) and (12), "AVE" represents the average value of the maximum output voltages V max of the gas sensor 2 and the water vapor sensor 1, and "σ" represents the standard deviation. The maximum output voltage V max refers to the amount of increase (maximum increase) before and after the exhalation.

Next, the threshold value calculation unit 521 checks whether the calculated threshold value TG is larger than a predetermined output voltage V max c (S429). The output voltage V max c is change in the output voltage of the gas sensor 2 or the water vapor sensor 1 when a gas other than exhalation (for example, a gas of 10 ppm of ethanol in a case of a calibration curve of the hydrogen sensor 22) is introduced. Such a voltage value is stored in advance in the storage device 602. The processing in step S429 prevents unauthorized use by setting the threshold values TG and Tw with a pseudo gas that is not exhalation.

As a result of step S429, if the calculated threshold value TG is equal to or smaller than the output voltage V max c on the calibration curve (S429→No), the threshold value calculation unit 521 returns the processing to step S422 and prompts introduction of exhalation and calculates the threshold values TG and Tw again.

As a result of step S429, if the calculated threshold value TG is larger than the predetermined output voltage V max c (S429→Yes), the threshold value calculation unit 521 sets the calculated threshold value TG and the threshold value Tw as new threshold values (S430). The calculated threshold value TG and threshold value Tw are stored in the storage device 602 in association with a user's ID. if the exhaled gas detection device A2 is used only by a specific user, respective threshold values included in the calculated threshold value TG and the threshold value Tw may not be associated with the ID.

Various gases may be adsorbed by the gas sensor 2 used for a long period of time.

After activation of the exhaled gas detection device A2 before the introduction of outside air (exhalation), whether the present output voltages VG1 and VG2 of the gas sensor 2 are equal to or larger than the threshold value TG is determined. With the determination, the exhaled gas detection device A2 prevents false detection due to adsorption of the gas in the gas sensor 2. Furthermore, the exhaled gas detection device A2 considers the gas sensor 2 to be in a gas-adsorbed state while the gas sensor is performing an output despite the fact that the outside air (exhalation) is not introduced, and has the adsorbed gas evaporated by heating with the heater 24.

Note that similar processing to steps S428 to S430 in FIG. 14 is performed to update the threshold value TG and the threshold value Tw performed in step S128 in FIG. 13.

Figure 15:
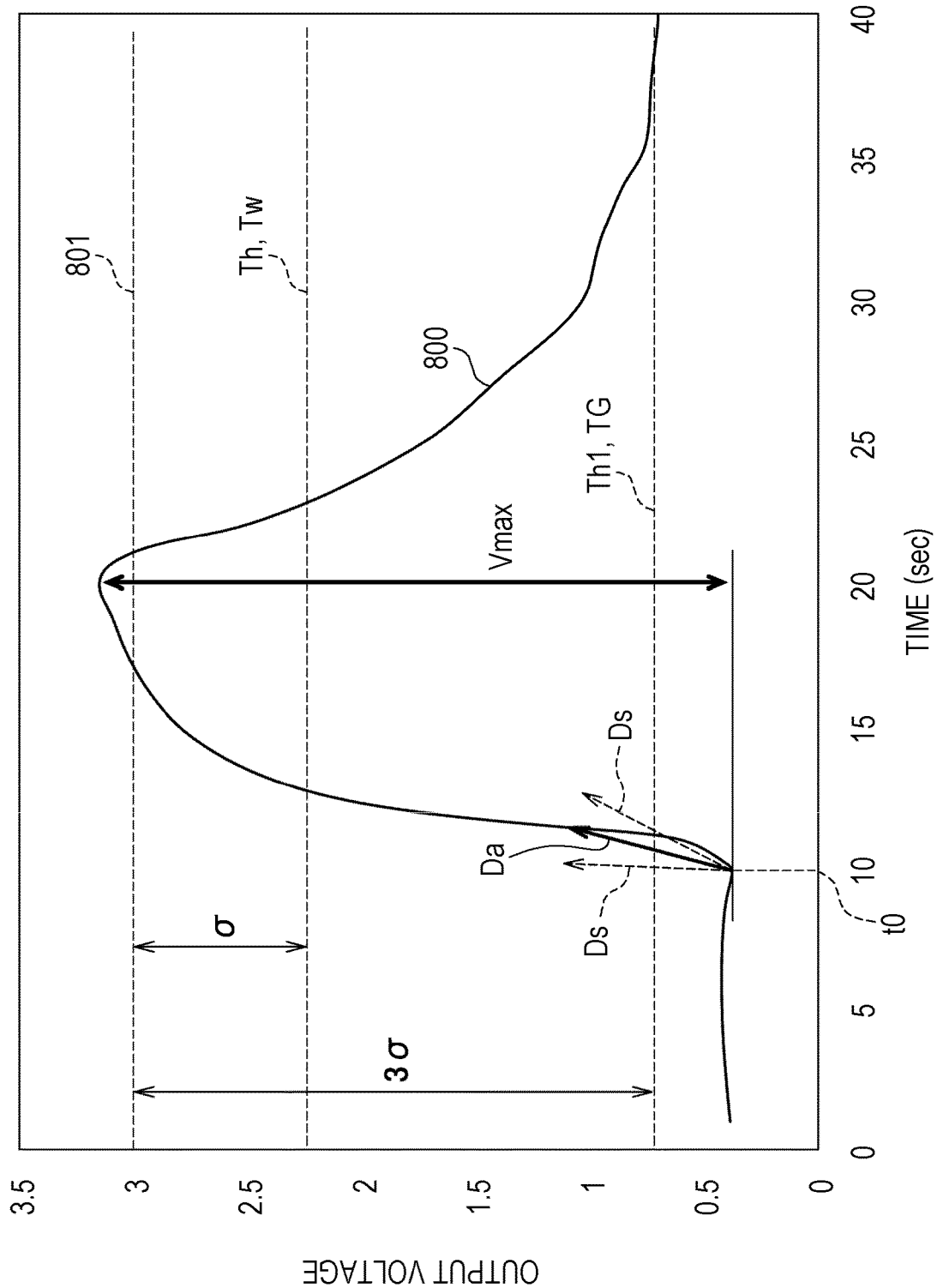
FIG. 15 is a graph for describing a threshold value setting method in a hydrogen sensor.

FIG. 15 is a graph for describing a method of setting the threshold value TG and the threshold value Tw in the hydrogen sensor.

Here, FIG. 15 illustrates an example of time change 800 in the output voltage of the hydrogen sensor 22. Note that reference numeral 800 represents time change in the output voltage of the hydrogen sensor 22 obtained in the first exhalation introduction.

Reference numeral 801 in FIG. 15 represents an average value AVE of the maximum output voltages V max of the hydrogen sensor 22.

Then, as illustrated in FIG. 15, the threshold value Th (Tw) is set to a value below the average value AVE (801) of the maximum output voltages V max by the standard deviation σ. Then, the threshold value Th1 (TG) is set to a value below the average value AVE (801) by the standard deviation σ×3. Symbols Da and Ds will be described below.

Figure 16:
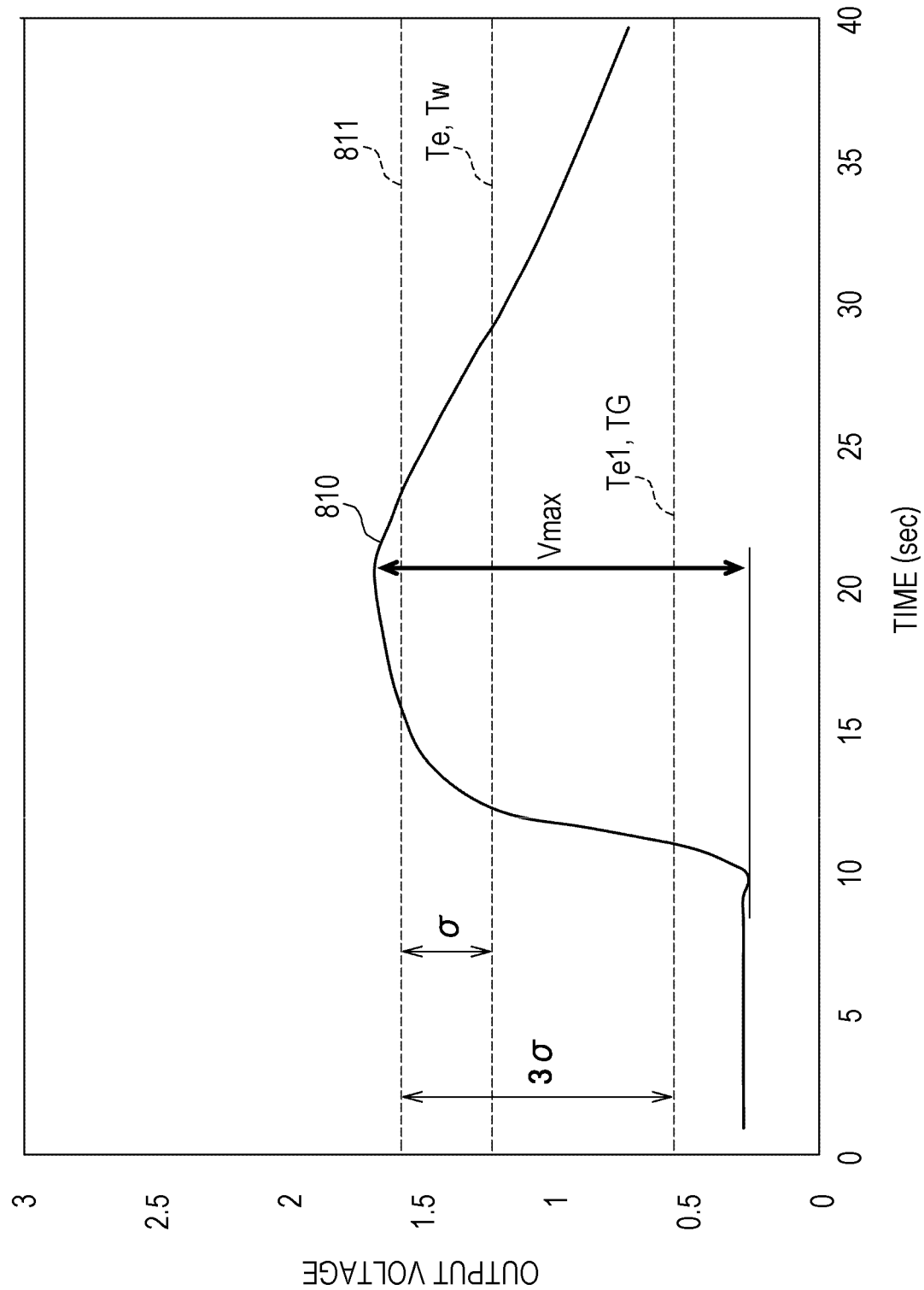
FIG. 16 is a graph for describing a threshold value setting method in an ethanol sensor.

FIG. 16 is a graph for describing a method of setting the threshold value TG and the threshold value Tw in the ethanol sensor.

Here, reference numeral 810 represents an example of time change in the output voltage of the ethanol sensor 21. Note that reference numeral 810 represents time change in the output voltage of the ethanol sensor 21 obtained in the first exhalation introduction.

Reference numeral 811 in FIG. 15 represents an average value AVE of the maximum output voltages V max of the ethanol sensor 21.

Then, as illustrated in FIG. 15, the threshold value Te (Tw) is set to a value below the average value AVE (811) of the maximum output voltages V max by the standard deviation σ. Then, the threshold value Te1(TG) is set to a value below the average value AVE (811) by the standard deviation σ×3.

Here, although the examples of the hydrogen sensor 22 and the ethanol sensor 21 have been described, the threshold value TG and the threshold value Tw are similarly set about the acetaldehyde sensor 23. Further, the threshold value Ts2 of the water vapor sensor 1 is set by a similar method to the threshold value Tw.

Here, if the value of the threshold value TG is too large, exhalation introduction becomes OK in an early stage of attenuation. As a result, exhalation is introduced in a state where the output voltage of the gas sensor 2 is not sufficiently lowered. As a result, the output voltage by the newly introduced exhalation is added to the output voltage of the gas sensor 2 that has not been sufficiently lowered. As a result, a large error occurs in the alcohol determination. On the contrary, if the threshold value TG is too small, it takes forever to become OK in exhalation introduction.

Further, if the threshold value Tw is too large, exhalation introduction will not be detected even though the exhalation is normally introduced. On the contrary, if the threshold value Tw is too small, a gas in ambient air will be detected as exhalation introduction even though exhalation is not introduced. In addition, it is necessary to consider individual differences in setting the threshold value Tw.

According to the present embodiment, appropriate threshold values TG and Tw in consideration of individual differences can be set.

Further, a threshold value regarding a rising slope of a signal may be set in addition to the threshold values TG and Tw. That is, the threshold value calculation unit 521 calculates the average value and the standard deviation of the maximum output voltages V max in step S427 in FIG. 14 and calculates slopes of signal values of the gas sensor 2 and the water vapor sensor 1 in a predetermined time from the exhalation introduction. This is referred to as the rising slope. Then, the threshold value calculation unit 521 calculates an average value Da and a standard deviation Ds of the rising slopes of when the exhalation is introduced multiple times (for example, three times) (see FIG. 15). Then, in steps S512 and S522 in FIG. 17, the false detection prevention unit 515 determines whether slopes at the rising of the signal values of the water vapor sensor 1 and the gas sensor 2 fall within a range of two standard deviations Ds. This determination is performed together with the processing described in step S512 and S522 in FIG. 17. If the slopes fall outside the range of two standard deviations Ds, the false detection prevention unit 515 determines that the introduced outside air is not exhalation of a person. In doing so, the accuracy of false detection prevention is improved.

(False Detection Prevention Processing)

Figure 17:
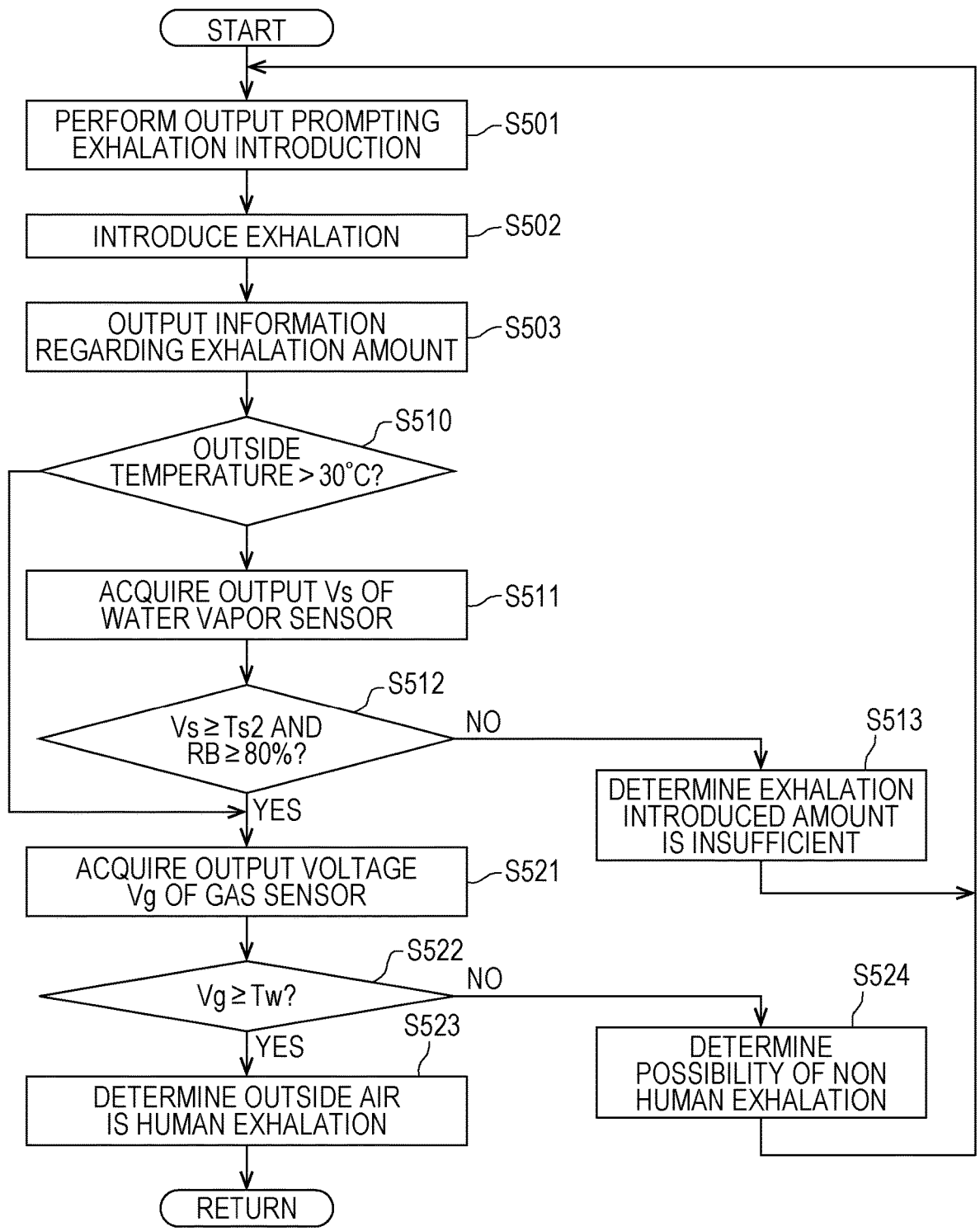
FIG. 17 is a flowchart illustrating a detailed processing procedure of false detection prevention processing according to the present embodiment.

FIG. 17 is a flowchart illustrating a detailed processing procedure of false detection prevention processing (S105 in FIG. 13) according to the present embodiment.

First, the output processing unit 519 performs the output prompting the user to introduce exhalation via the output device 603 (display device 31) (S501), and outside air (exhalation) is introduced through the introduction section 33 (S502).

The output processing unit 519 has the output device 603 output information regarding the introduced exhalation introduction amount (S503). The output here is performed by a display with the indicator 32, a sound emitted from the speaker 32a, or the like.

Next, the false detection prevention unit 515 determines whether outside temperature acquired from an outside temperature sensor (not illustrated) is higher than 30° C. (S510).

As a result of step S510, when the outside temperature is higher than 30° C. (S510→Yes), the processing proceeds to step S521. That is, determination of false detection is performed only with the output voltage of the gas sensor 2 without using the output voltage of the water vapor sensor 1. This is because the water vapor in the exhalation on the surface of the water vapor sensor 1 tends to less likely adhere (condense) to the insulation 13 of the water vapor sensor 1 when the outside temperature exceeds 30° C. In the present embodiment, when the outside temperature is higher than 30° C., the determination of false detection is performed without using the output voltage of the water vapor sensor 1. However, the temperature is not limited to 30° C. as long as water vapor in the exhalation no longer adheres to the insulation 13 of the water vapor sensor 1 at the temperature. Further, the temperature may be a substrate temperature of the exhalation detector A1 or a temperature around the exhalation detector A1 instead of the outside temperature.

As a result of step S510, when the outside temperature is equal to or lower than 30° C. (S510→No), the false detection prevention unit 515 acquires the output voltage Vs of the water vapor sensor 1 (S511).

Then, the false detection prevention unit 515 determines whether the output voltage Vs of the water vapor sensor 1 is equal to or larger than the threshold value Ts2 (Vs≥Ts2) and the peak frequency ratio RB≥80% (S512).

Here, the peak frequency ratio RB will be described with reference to FIG. 18.

Figure 18:
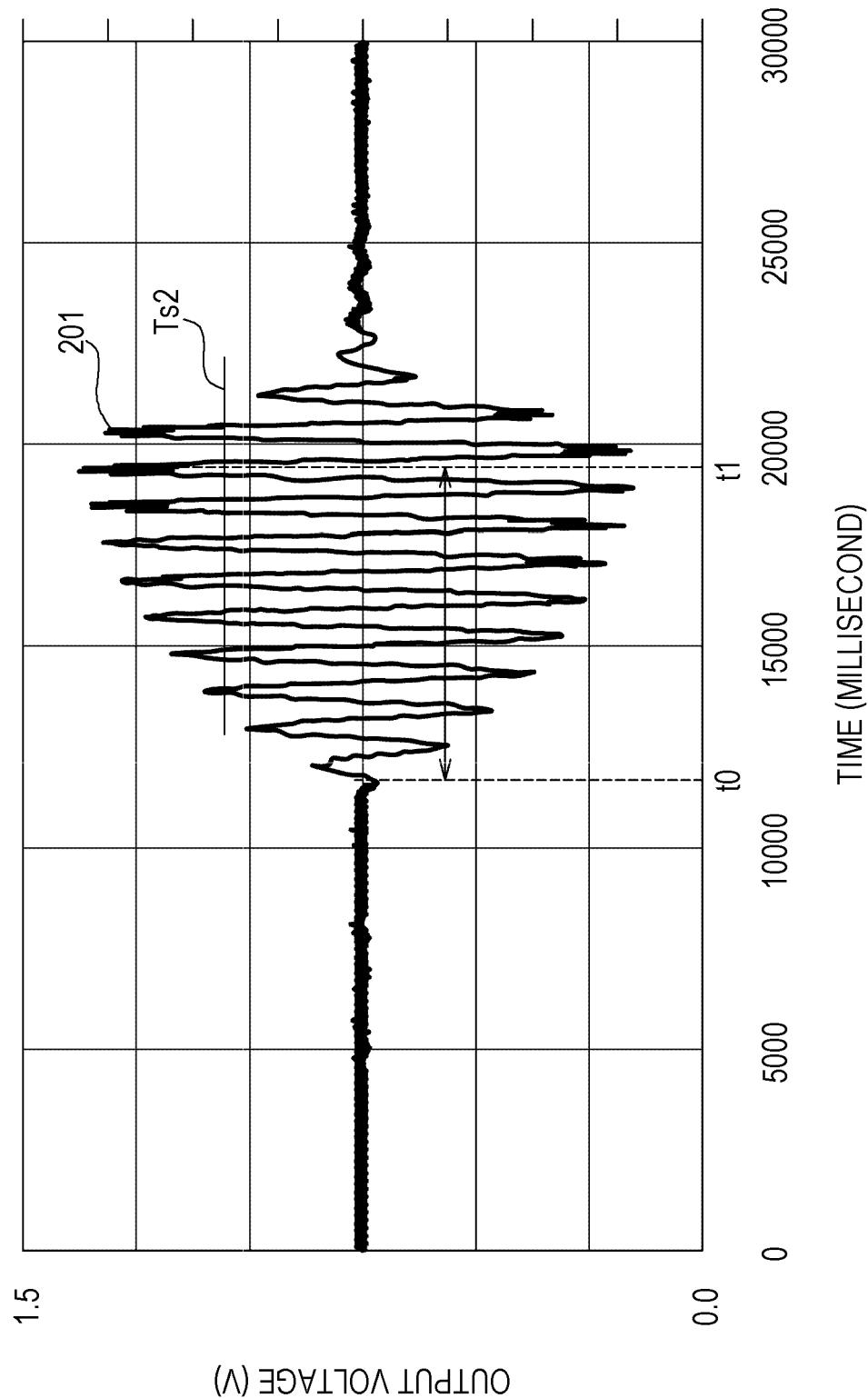
FIG. 18 is a graph for describing a peak frequency ratio.

In FIG. 18, the horizontal axis represents time and the vertical axis represents the output voltage of the water vapor sensor 1.

As illustrated in FIG. 18, an output voltage 201 of the water vapor sensor 1 has an alternating waveform. This is because the voltage input to the water vapor sensor 1 is an alternating voltage as illustrated in FIG. 2.

Here, t0 in FIG. 18 represents a time when the outside air (exhalation) has been introduced. Then, a time when a predetermined time has elapsed since the introduction of the outside air (exhalation) is t1. Further, the threshold value Ts2 is set as illustrated in FIG. 18.

Here, the false detection prevention unit 515 counts the number of peaks in the output voltage of the water vapor sensor 1 from time t0 to time t1. This number is P1. In the example in FIG. 18, P1=9.

Further, the false detection prevention unit 515 counts the number of peaks in the output voltage of the water vapor sensor 1 to the time t1 after the peak of the output voltage of the water vapor sensor 1 exceeds the threshold value Ts2. This number is P2. In the example in FIG. 18, P2=7.

Then, RB is defined by the following expression (1).

$$RB = (P2/P1) \times 100 \quad (1)$$

In step S512 in FIG. 17, whether RB expressed by the expression (1) is equal to or larger than 80(%) is determined. Incidentally, in the example in FIG. 18, P1=9 and P2=7, and therefore RB≈77(%) and "No" is selected in step S521.

Returning to the description of FIG. 17.

As a result of step S512, in a case where the output voltage Vs of the water vapor sensor 1 is less than the threshold value Ts2 or RB<80% (S512→No), the false detection prevention unit 515 determines that the exhalation introduction amount (i.e, exhalation strength) is insufficient (S513) and returns the processing to step S501. As a result, remeasurement of exhalation is prompted.

As a result of step S512, if the output voltage Vs of the vapor sensor is equal to or larger than the threshold value Ts2 and RB≥80% (S512→Yes), the false detection prevention unit 515 acquires an output voltage Vg of the gas sensor 2 (S521). Here, the output voltage Vg is output voltages of the ethanol sensor 21, the hydrogen sensor 22, and the acetaldehyde sensor 23. The output voltage of the ethanol sensor 21 obtained here is Ve, the output voltage of the acetaldehyde sensor 23 is Va, and the output voltage of the hydrogen sensor 22 is Vh.

Next, the false detection prevention unit 515 determines whether the acquired output voltage Vg of the gas sensor 2 is equal to or larger than a predetermined threshold value Tw (first threshold value) (Vg≥Tw) (S522). Here, the output voltage Vg of the gas sensor 2 being equal to or larger than the threshold value Tw means that the output voltage of the ethanol sensor 21 is equal to or larger than the threshold value Te (see FIG. 9), the output voltage of the acetaldehyde sensor 23 is equal to or larger than the threshold value Ta (see FIG. 9), and the output voltage of the hydrogen sensor 22 is equal to or larger than the threshold value Th (see FIG. 9). Note that determination in step S522 may be made on the basis of the output voltage of the ethanol sensor 21 being equal to or larger than the threshold value Te, the output voltage of the acetaldehyde sensor 23 being equal to or larger than the threshold value Ta, or the output voltage of the hydrogen sensor 22 being equal to or larger than the threshold value Th. Alternatively, determination of "Yes" may be made in step S522 when at least two of the output voltage of the ethanol sensor 21 being equal to or larger than the threshold value Te, the output voltage of the acetaldehyde sensor 23 being equal to or larger than the threshold value Ta, and the output voltage of the hydrogen sensor 22 being equal to or larger than the threshold value Th are established.

As a result of step S522, if the output voltage Vg of the ethanol sensor 21 is equal to or larger than the predetermined threshold value Tw (S522→Yes), the false detection prevention unit 515 determines that the introduced outside air is exhalation of a person (S523). Thereafter, the processing unit 511 returns the processing to step S111 in FIG. 14.

As a result of step S522, if the output voltage Vg of the ethanol sensor 21 is less than the predetermined threshold value Tw (S522→No), the false detection prevention unit 515 determines that there is a possibility that the introduced outside air is not exhalation of a person (S524). Then, the false detection prevention unit 515 returns the processing to step S501 to prompt remeasurement of exhalation.

Note that, as described above, in the processing in step S522, the false detection prevention unit 515 determines whether the introduced outside air is exhalation of a person according to the same logic as the determination as to whether a gas adheres to the gas sensor 2 in step S403 in FIG. 14.

Determination in step S522 in FIG. 17 will be described with reference to FIG. 19.

Figure 19:
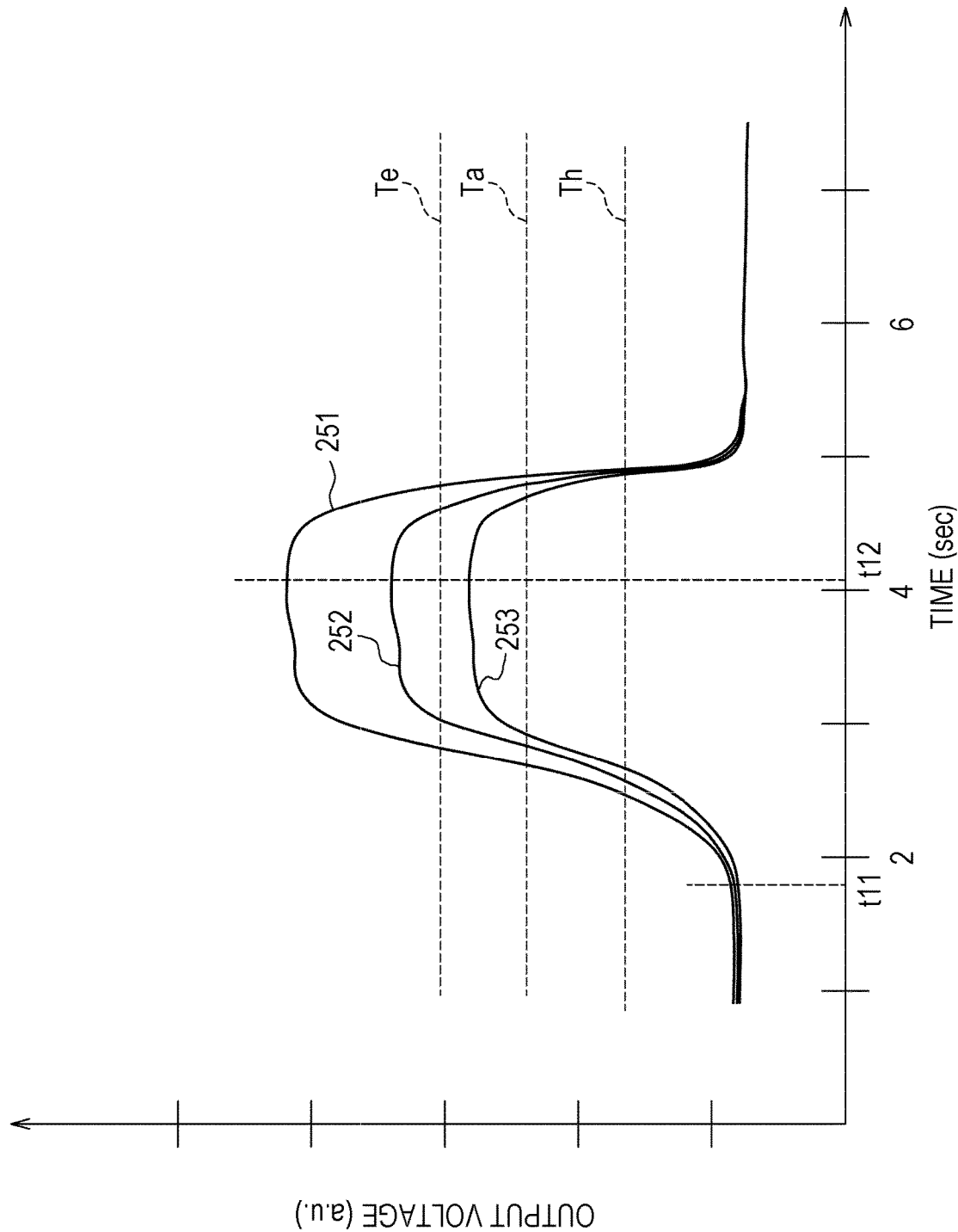
FIG. 19 is a graph for describing determination in step S522 in FIG. 17.

FIG. 19 is a diagram illustrating an example of the time change in the output voltages of the ethanol sensor 21, the hydrogen sensor 22, and the acetaldehyde sensor 23. Here, FIG. 19 illustrates time change 251 in the output voltage of the ethanol sensor 21 and time change 252 in the output voltage of the acetaldehyde sensor 23. FIG. 19 illustrates time change 253 in the output voltage of the hydrogen sensor 22.

In FIG. 19, the horizontal axis represents time and the vertical axis represents the output voltages (arbitrary unit) of the ethanol sensor 21, the hydrogen sensor 22, and the acetaldehyde sensor 23.

In FIG. 19, a time t11 is a time when introduction of outside air (exhalation) is started, and a time t12 is a time when introduction of the outside air (exhalation) is completed.

As illustrated in FIG. 19, when introduction of the outside air (exhalation) is started, the output voltages 251 to 253 of the ethanol sensor 21, hydrogen sensor 22, and acetaldehyde sensor 23 start to rise, and when the introduction of the outside air (exhalation) is completed, the output voltages descend over predetermined time.

Further, the threshold value Te for the output voltage 251 of the ethanol sensor 21, the threshold value Ta for the output voltage 252 of the acetaldehyde sensor 23, and the threshold value Th for the output voltage 253 of the hydrogen sensor 22 are provided.

In step S522 in FIG. 17, whether the output voltage 251 of the ethanol sensor 21 is equal to or larger than the predetermined threshold value Te, the output voltage 252 of the acetaldehyde sensor 23 is equal to or larger than the predetermined threshold value Ta, and the output voltage 253 of the hydrogen sensor 22 is equal to or larger than the predetermined threshold value Th are determined. Thereby, whether the introduced outside air is exhalation of a person is determined.

As described above, the exhalation of a person contains ethanol, acetaldehyde, and hydrogen in trace amounts even if the person has not been drinking. In the present embodiment, the threshold value Te for the output voltage 251 of the ethanol sensor 21, the threshold value Ta for the output voltage 252 of the acetaldehyde sensor 23, and the threshold value Th for the output voltage 253 of the hydrogen sensor 22 are set to values detectable while the user has not been drinking. With the setting, whether the introduced outside air is exhalation of a person is made detectable.

According to the exhaled gas detection device A2 of the present embodiment, accuracy of determination as to whether the introduced outside air is exhalation of a person can be improved by performing double check with the water vapor sensor 1 and the gas sensor 2. In particular, since exhalation of a person is saturated water vapor with the humidity of 100% regardless of individual differences or physical conditions, the exhaled gas detection device A2 according to the present embodiment can perform exhalation determination with high accuracy regardless of individual differences or physical conditions.

Further, according to the exhaled gas detection device A2 of the present embodiment, the condensation avoidance processing and the gas sensor initialization processing are performed. As a result, abnormality detection at the time of activation of the exhaled gas detection device A2 and recovery from the abnormality become possible.

Even if the water vapor sensor 1 of the present embodiment is replaced with an existing humidity sensor, the humidity sensor measures humidity and thus response is slow, so instant determination as to whether the outside air introduced into the exhaled gas detection device A2 is exhalation is difficult. Further, an upper limit of measurable humidity of the humidity sensor is 80% to 90%, and the humidity sensor is not suitable for detecting exhalation of a person, which is saturated water vapor.

Then, if the alcohol concentration (ethanol concentration) based on the output voltage of the gas sensor 2 is equal to or larger than the reference value Cs in step S121 in FIG. 13, the exhaled gas detection device A2 according to the present embodiment determines that the user has been drinking. The determination enhances the accuracy of the determination of drinking or non-drinking.

Further, as illustrated in step S512 in FIG. 17, the exhaled gas detection device A2 determines whether the output voltage Vs of the water vapor sensor 1 is equal to or larger than the threshold value Ts2 (Vs≥Ts2) and the peak frequency ratio RB≥80%. With the determination, the accuracy of the determination as to whether the outside air is exhalation can be improved.

[Another System Example]

Figure 20:
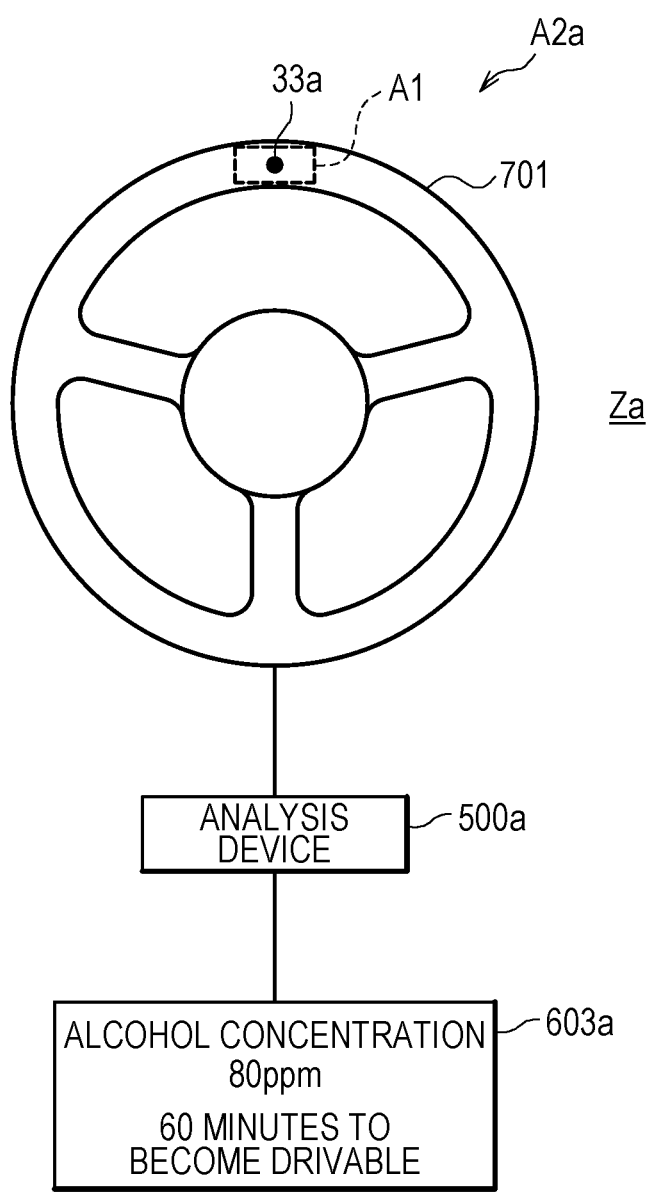
FIG. 20 is a diagram illustrating another configuration example of the exhalation measurement system according to the present embodiment.

FIG. 20 is a diagram illustrating another configuration example of the exhalation measurement system according to the present embodiment.

FIG. 20 illustrates an example in which an exhalation measurement system Za is provided in a vehicle.

In the exhalation measurement system Za, the exhalation detection device A1 is installed in a steering 701 provided with an introduction section 33a. In this case, the steering 701 is the housing 30 (see FIGS. 7 and 8). Then, the processing illustrated in FIGS. 13 to 17 is performed by an analysis device 500a installed in the vehicle. The configuration of the analysis device 500a is similar to that illustrated in FIG. 19.

Then, a processing result in the analysis device 500a is displayed on a display device 603a. Content displayed on the display device 603a is the content displayed on the display device 31 in FIG. 7 or the content displayed on the portable device A3.

Note that the present embodiment assumes that the exhaled gas detection device A2 is used to determine drinking or non-drinking during vehicle operation, but the use of the exhaled gas detection device A2 is not limited to this example. For example, the exhaled gas detection device A2 may be used for medical purposes. In this case, measurement of exhalation by the exhaled gas detection device A2 is performed at home, the measurement value is transmitted to a medical institution via a network, and analysis of a gas in the exhalation may be performed in the medical institution. In this case, sensors other than the ethanol sensor 21, the hydrogen sensor 22, and the acetaldehyde sensor 23 may be used as the sensors included in the gas sensor 2.

Further, the exhaled gas detection device A2 in the present embodiment includes the exhalation detection device A1 (see FIG. 1) in the housing 30 (see FIGS. 7 and 8), and the user introduces exhalation through the introduction section 33 (see FIGS. 7 and 8). However, the configuration is not limited thereto. For example, the user may directly blow into the exhalation detection device A1 while the exhalation detection device A1 is exposed. Alternatively, the housing 30 may be provided with a lid, and when the user opens the lid, the exhalation detection device A1 is exposed and the user may blow into the exhalation detection device A1.

Figure 21:
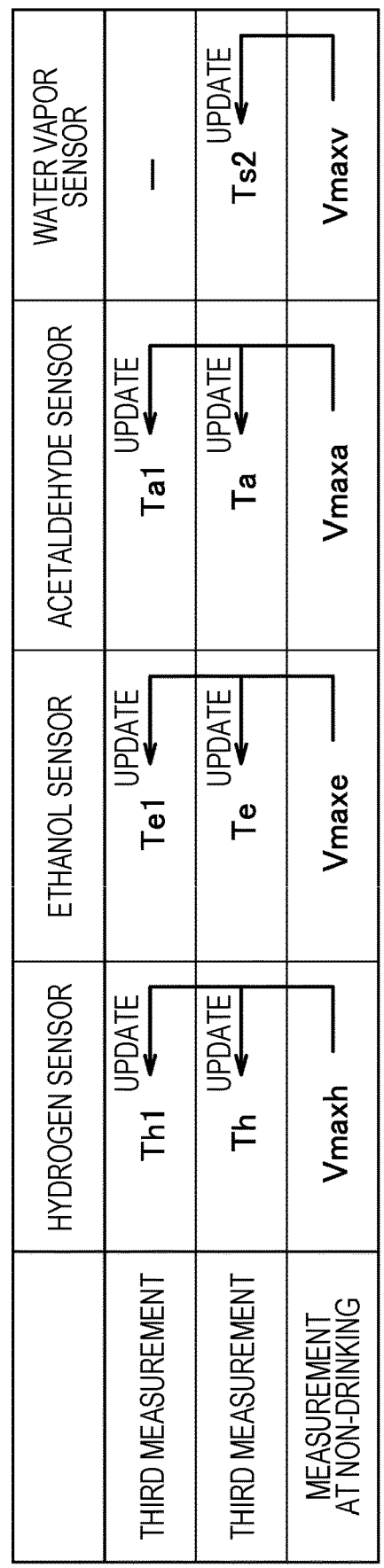
FIG. 21 is a diagram illustrating explanation of updating of threshold value TG and threshold value Tw.

FIG. 21 is a diagram illustrating description of updating of threshold value TG and threshold value Tw. FIG. 21 illustrates the updating processing in step S128 in FIG. 13.

FIG. 21 illustrates updating of the threshold values of the hydrogen sensor 22, the ethanol sensor 21, the acetaldehyde sensor 23, and the water vapor sensor 1.

As described above, the threshold value Th1 of the hydrogen sensor 22, the threshold value Te1 of the ethanol sensor 21, and the threshold value Ta1 of the acetaldehyde sensor 23 are included in the threshold value TG.

Similarly, the threshold value Th of the hydrogen sensor 22, the threshold value Te of the ethanol sensor 21, the threshold value Ta of the acetaldehyde sensor 23, and the threshold value Ts2 of the water vapor sensor 1 are included in the threshold value Tw.

Such updating may be performed every time or may be performed every plurality of times (for example, three times). If the updating is performed every time, the latest three times of data may be used.

As illustrated in FIG. 21, the threshold values Th1 and Th of the hydrogen sensor 22 are updated using a maximum output voltage V max h of the hydrogen sensor 22 acquired in step S122a. Similarly, the threshold values Te1 and Te of the ethanol sensor 21 are updated using a maximum output voltage V max e of the ethanol sensor 21 acquired in step S122a. Furthermore, the threshold values Ta1 and Ta of the acetaldehyde sensor 23 are updated using a maximum output voltage V max a of the acetaldehyde sensor 23 acquired in step S122a. Then, the threshold value Ts2 of the water vapor sensor 1 is updated using a maximum output voltage V max v of the water vapor sensor 1 acquired in step S122a.

Calculation of the threshold values is performed by a technique based on FIG. 15 and the like.

By continuously updating the threshold values in this way, setting of the threshold values TG and Tw in consideration of the physical conditions and the like changing from day to day can be performed.

Second Embodiment

Figure 22:
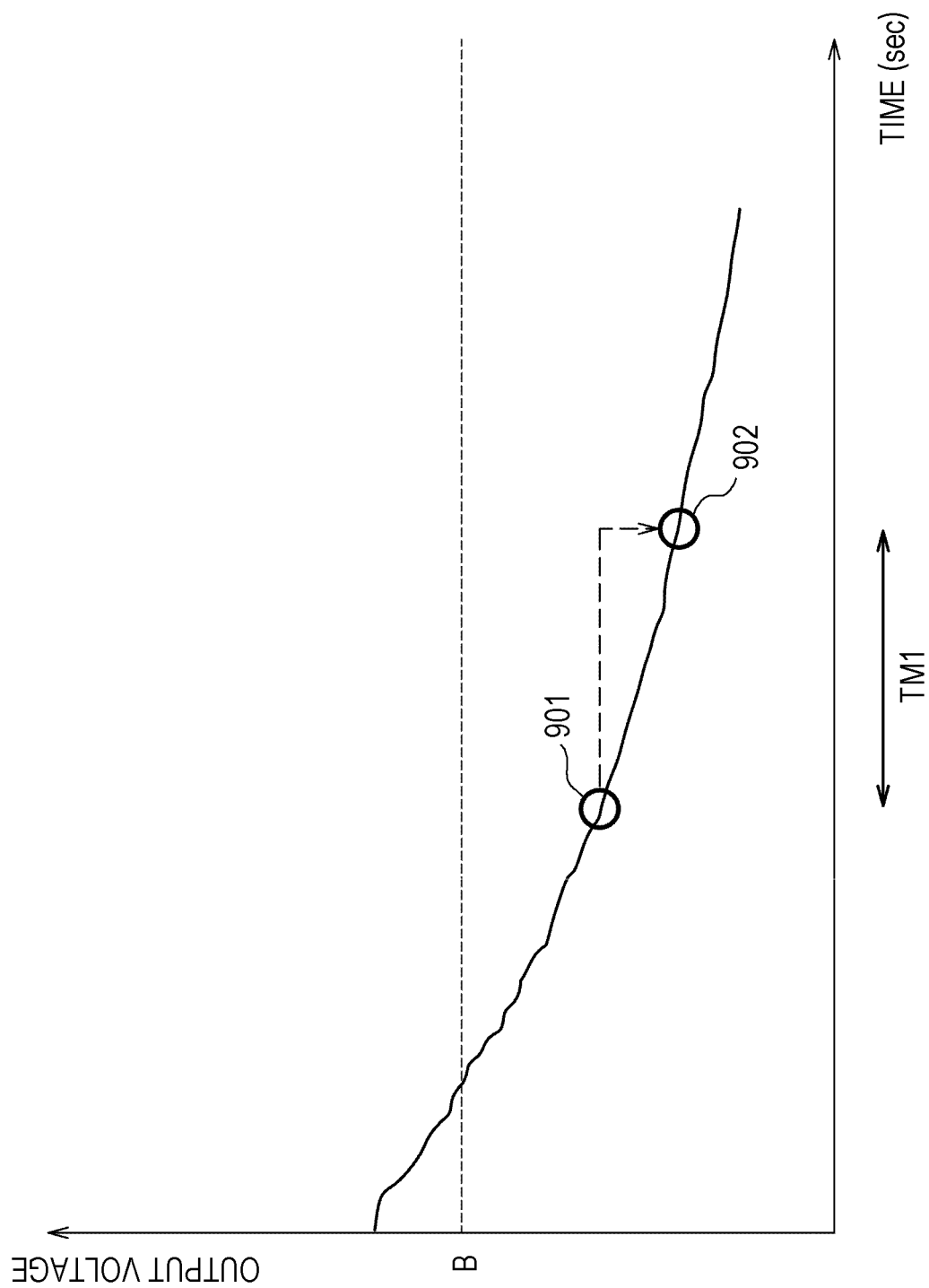
FIG. 22 is a graph illustrating a threshold value determination technique in a second embodiment.

FIG. 22 is a graph illustrating a technique for determining the threshold value TG and the threshold value Tw in the second embodiment.

In FIG. 22, the horizontal axis represents time and the vertical axis represents the output voltage of the sensor. Here, the sensor is a water vapor sensor 1 or a gas sensor 2.

Further, in FIG. 22, a broken line indicates a predetermined threshold (fourth threshold) B.

In the second embodiment, a threshold value calculation unit 521 calculates a threshold value TG on the basis of a value of when the following two conditions are satisfied for a signal voltage acquired by single exhalation introduction.

(B1) An output voltage of the sensor is a value equal to or smaller than the threshold value B in an attenuation period. The threshold value B is, for example, a voltage value corresponding to the gas concentration of 10 ppm. Incidentally, the gas concentration of 10 ppm is a value resulting from no influence of a baseline noise.

(B2) An attenuation rate is equal to or smaller than a predetermined value. The attenuation factor is, for example, (an output voltage 901—an output voltage 902)/a time TM1 in FIG. 22. For example, 1% can be considered as the predetermined value.

When the conditions of (B1) and (B2) are satisfied, the threshold value calculation unit 521 sets the output voltage 902 in FIG. 22 as the threshold value TG.

In the second embodiment, a threshold value Tw may be determined by the above technique described in the first embodiment or may be set according to a maximum output voltage V max obtained by single exhalation measurement (that is, the technique of the second embodiment). In this case, the threshold values TG and Tw in consideration of individual differences can be calculated by single exhalation introduction.

Third Embodiment

Next, installation of a sensor Se will be described with reference to FIGS. 23 to 25.

The sensor Se is a water vapor sensor 1, a gas sensor 2, and the like. Incidentally, it has been confirmed that series connection of the plurality of sensors Se is favorable in terms of sensitivity and stability.

Figure 23:
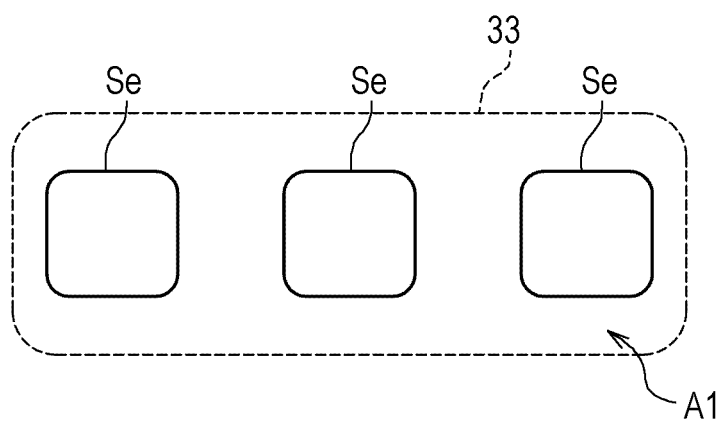
FIG. 23 is a view illustrating installation of a conventional sensor.

FIG. 23 is a top view of a peripheral part of an exhalation detection device A1 so far.

Further, as illustrated in FIG. 23, the sensor Se is installed below an introduction section 33.

In such a configuration, exhalation introduced through the introduction section 33 flows around the sensor Se. As a result, the sensitivity of the sensor Se is reduced.

Change in physical condition can be read from variation in daily output voltages of the plurality of (here, three) sensors Se of a non-drinking time.

Figure 24A:
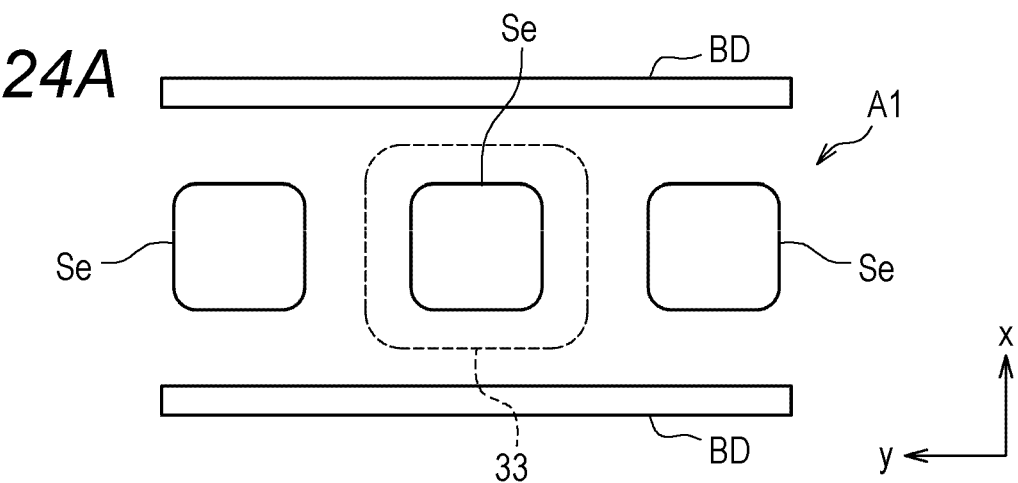
FIG. 24A is a top view (part 1) of a peripheral part of an exhalation detection device in a third embodiment.
Figure 24B:
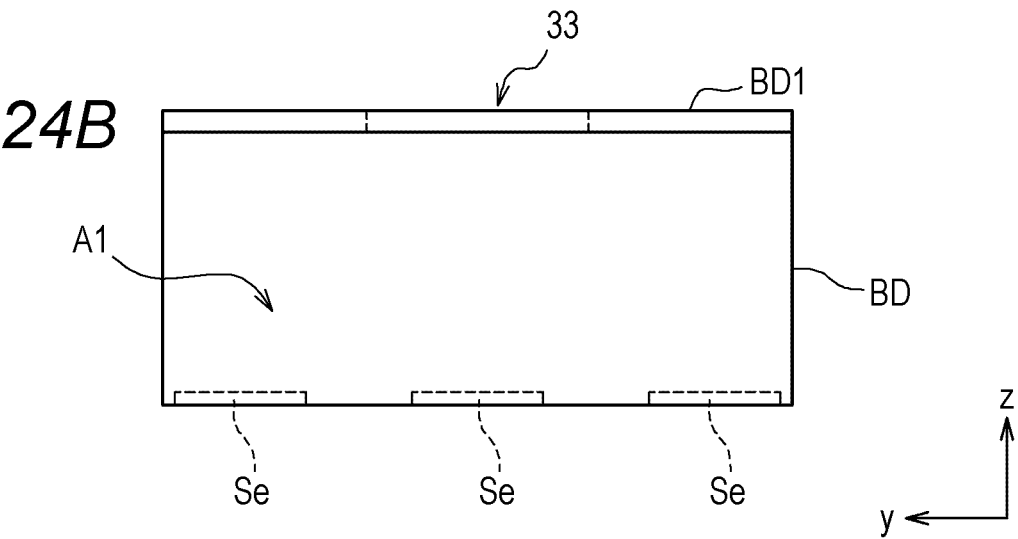
FIG. 24B is a side view of the peripheral part of the exhalation detection device in the third embodiment.

FIG. 24A is a top view of a peripheral part of an exhalation detection device A1 in the third embodiment, and FIG. 24B is a side view of the peripheral part of the exhalation detection device A1 in the third embodiment.

In the peripheral part of the exhalation detection device A1 illustrated in FIGS. 24A and 24B, a plate-like portion BD is installed in a z-axis direction with respect to the sensor Se. The installation of such a plate-like portion BD prevents the exhalation introduced through the introduction section 33 from flowing around. Thereby, the sensitivity of the sensor Se can be kept favorable. Moreover, as illustrated in FIG. 24B, a top plate BD1 with the introduction section 33 open is provided above the sensor Se.

Furthermore, in the examples illustrated in FIGS. 24A and 24B, the introduction section 33 is smaller than the introduction section 33 illustrated in FIG. 23 and is provided directly above the middle sensor Se. Such a configuration has the exhalation concentrated and applied to the sensor Se.

Figure 25:
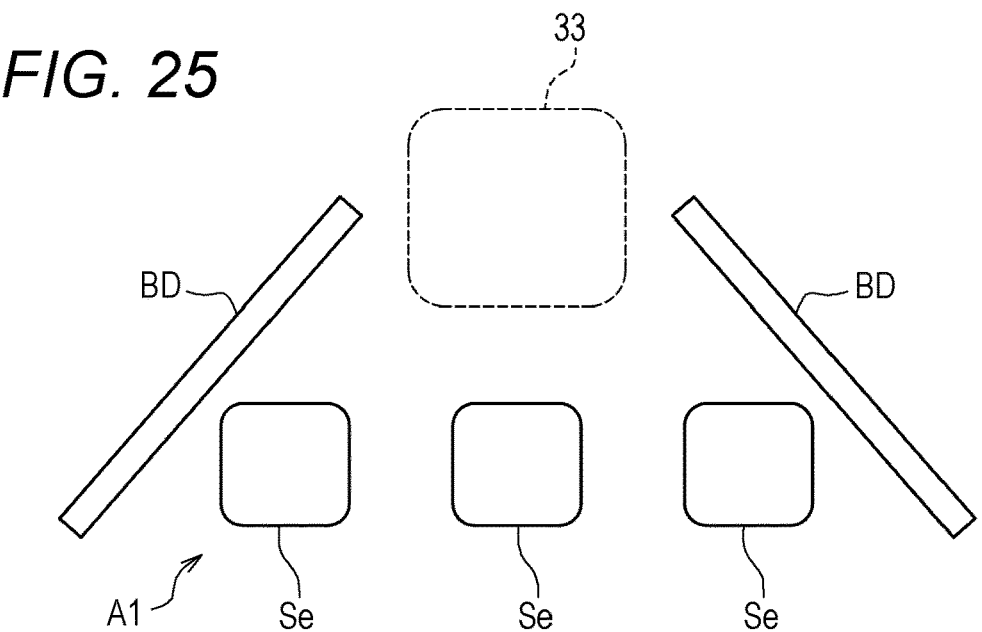
FIG. 25 is a top view (part 2) of the peripheral part of the exhalation detection device in the third embodiment.

FIG. 25 is a top view illustrating another example of the peripheral part of the exhalation detection device A1 in the third embodiment.

Further, in the view illustrated in FIG. 25, the plate-like portions BD are installed to form a mountain shape with the introduction section 33 at the top. Then, the sensors Se are arranged at the bottom of the mountain shape.

With such a configuration, the exhalation introduced through the introduction section 33 flows in a direction of the sensors Se along the plate-like portions BD. Thereby, the exhalation is equally applied to the three sensors Se.

Fourth Embodiment

Figure 26:
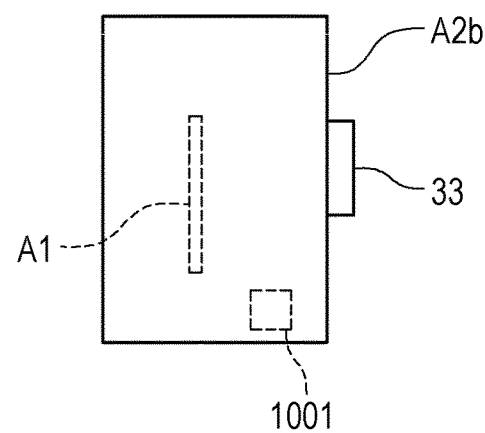
FIG. 26 is a view (part 1) illustrating an exhaled gas detection device in a fourth embodiment.

FIG. 26 is a view illustrating an exhaled gas detection device A2b in a fourth embodiment.

The exhaled gas detection device A2b includes an exhaust section 1001 for exhausting air around an exhalation detection device A1. Note that the exhaled gas detection device A2b has a mode in which a user holds the introduction section 33 in the mouth.

If outside air not originating from the user is accumulated in a housing of the exhaled gas detection device A2b, the outside air is unlikely to be discharged to the outside. In such a state, even if the user introduces exhalation, there is a possibility that the air around a water vapor sensor 1 or a gas sensor 2 is not replaced by the exhalation of the user. Alternatively, there is a possibility that the outside air originating from the outside other than the user and exhalation originating from the user are mixed.

In the example in FIG. 26, the exhaust section 1001 discharges the air originating from the outside of the user around the exhalation detection device A1. With the discharge of the air, air in the user's oral cavity is introduced around the exhalation detection device A1. By including the exhaust section 1001 in this manner, the air originating from the outside of the user around the exhalation detection device A1 can be quickly replaced with the air in the user's oral cavity.

With the configuration, the user can introduce the air in the user's oral cavity into around the exhalation detection device A1 without consciously blowing in the exhalation with the mouth simply holding the introduction section 33 of the exhaled gas detection device A2b.

Figure 27:
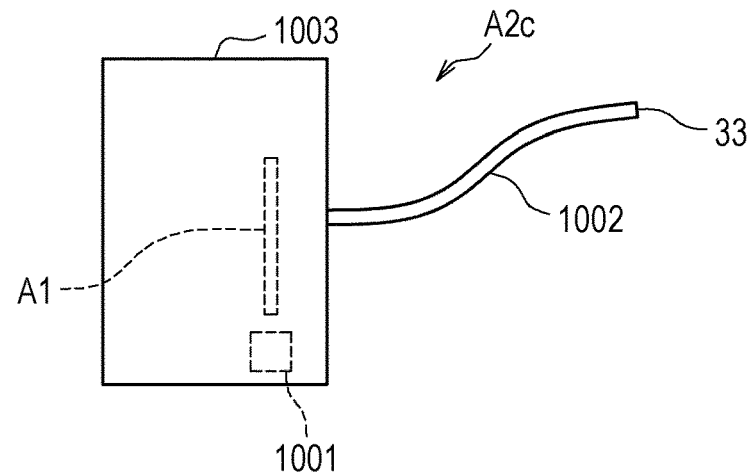
FIG. 27 is a view (part 2) illustrating the exhaled gas detection device in the fourth embodiment.

FIG. 27 is a view illustrating an exhaled gas detection device A2c having the introduction section 33 and a main body 1003 connected via a pipe 1002.

The exhaled gas detection device A2c as illustrated in FIG. 27 includes an exhaust section 1001. With the configuration, the user can introduce the air in the user's oral cavity into around the exhalation detection device A1 without consciously blowing in the exhalation with the mouth simply holding the introduction section 33 of the exhaled gas detection device A2c.

Note that the present invention is not limited to the above-described embodiments and includes various modifications. For example, the above embodiments have been described in detail for describing the present invention in an easy-to-understand manner, and the present invention is not necessarily limited to one including all the described configurations. Further, another configuration can be added to/deleted from/replaced with a part of the configurations of the present embodiments.

Further, a part or all of the above-described configurations, functions, the processing unit 511, the units 512 to 521, the storage devices 505 and 602, and the like may be achieved with hardware which is designed with an integrated circuit or the like. Further, as illustrated in FIG. 12, the above-described configurations, functions, and the like may be achieved with software in such a manner that a processor such as a CPU interprets and executes programs that implement the functions. Information such as programs, tables, and files that implement the functions can be stored in a memory, a recording device such as a solid state drive (SSD), or a recording medium such as an integrated circuit (IC) card, a secure digital (SD) card, or a digital versatile disc (DVD), other than being stored in the storage device 505 as illustrated in FIG. 12.

Further, in the embodiments, control lines and information lines necessary for the description have been illustrated, and not all the control lines and information lines for a product are necessarily illustrated. It may be considered that almost all the configurations are actually connected with one another.

What is claimed is:

1. An exhaled gas detector comprising:
   a gas detection element configured to measure concentration of a specific gas;
   an analysis unit configured with a processor to analyze a signal output from the gas detection element; and
   an output unit configured to output a result analyzed by the analysis unit, wherein
   the processor of the analysis unit is configured to:
   control the gas detection element to measure the specific gas in an exhalation of a non-drinking time and generate a first reference signal value for the exhalation;
   calculate, on the basis of the first reference signal value, a first threshold value for determining whether a signal value from the gas detection element indicates exhalation of a person;
   control the gas detection element to measure the specific gas in an inspection gas and generate a first measurement signal value for the inspection gas; and
   determine that the inspection gas is identified with an exhalation of a person upon determining that the first measurement signal value has exceeded the first threshold value.

2. The exhaled gas detector according to claim 1, further comprising:
   a water vapor detection element configured to detect whether the inspection gas contains saturated water vapor, wherein
   the processor of the analysis unit is configured to:
   control the water vapor detection element to measure water vapor in an exhalation of the non-drinking time and generate a second reference signal value for the exhalation;
   calculate, on the basis of the second reference signal value, a second threshold value for determining whether a signal value from the water vapor detection element indicates exhalation of a person;
   control the water vapor detection element to measure the inspection gas and generate a second measurement signal value for the inspection gas; and
   determine that the inspection gas is identified with the exhalation of a person upon determining that the second measurement signal value has exceeded the second threshold value.

3. The exhaled gas detector according to claim 1, wherein the processor of the analysis unit is further configured to:
   calculate a second threshold value for determining whether the gas adheres to the gas detection element on the basis of the first reference signal value, and
   operate a heater provided in the gas detection element until the first measurement signal value is equal to or larger than the second threshold value before determining whether the inspection gas is identified with the exhalation of a person.

4. The exhaled gas detector according to claim 3, wherein the first threshold value and the second threshold value calculated by the processor of the analysis unit are calculated on the basis of exhalations actually used.

5. The exhaled gas detector according to claim 3, wherein the processor of the analysis unit is further configured to:
   calculate for the exhalations actually used an average value and a standard deviation of maximum signal values that are maximum values of the first reference signal values from the gas detection element, and calculates the first threshold value and the second threshold value on the basis of the standard deviation.

6. The exhaled gas detector according to claim 3, wherein the processor of the analysis unit is further configured to:
   store a maximum first reference signal value from the gas detection element and update the first threshold value and the second threshold value on the basis of the stored maximum first reference signal value, when the inspection gas is identified with exhalation of a person, and non-drinking is determined as a result of drinking determination conducted afterward.

7. The exhaled gas detector according to claim 1, wherein the processor of the analysis unit is further configured to:
   calculate a second threshold value on the basis of information about a rising slope of the first reference signal value from the gas detection element, and
   determine whether the inspection gas exposed to the gas detection element is exhalation of a person on the basis of the first threshold value and the second threshold value.

8. The exhaled gas detector according to claim 1, wherein the processor of the analysis unit is further configured to:
   calculate an attenuation rate of the first measurement signal value in a predetermined period if the first measurement signal value is equal to or smaller than a second threshold value during attenuation of the first measurement signal value from the gas detection element, and sets as the first threshold value the first measurement signal value having the attenuation rate equal to or smaller than a predetermined value.

9. An exhaled gas detection method comprising the steps of:
   measuring, by a gas detection element, the specific gas in an exhalation of non-drinking time to generate a first reference signal for the exhalation;
   calculating, by a processor of an analysis unit, on the basis of the first reference signal value, a first threshold value for determining whether a signal value from the gas detection element indicates exhalation of a person;
   measuring, by the gas detection element, the specific gas in an inspection gas to generate a first measurement signal value for the inspection gas; and
   determining, by the processor of the analysis unit, that the inspection gas is identified with an exhalation of a person upon determining that the first measurement signal value has exceeded the first threshold value.

10. The exhaled gas detection method according to claim 9, further comprising the steps of:
    measuring, by a water vapor detection element, water vapor in an exhalation of non-drinking time and generate a second reference signal value for the exhalation;
    calculating, on the basis of the second reference signal value, a second threshold value for determining whether a signal value from the water vapor detection element indicates exhalation of a person;
    measuring, by the water vapor detection element, the inspection gas and generate a second measurement signal value for the inspection gas; and
    determining that the inspection gas is identified with the exhalation of a person upon determining that the second measurement signal value has exceeded the second threshold value.

11. The exhaled gas detection method according to claim 9, further comprising the steps of:
    calculating a second threshold value for determining whether the gas adheres to the gas detection element on the basis of the first reference signal value; and operating a heater provided in the gas detection element until the first measurement signal value is equal to or larger than the second threshold value before determining whether the inspection gas is identified with the exhalation of a person.

* * * * *